United States Patent [19]
Fujioka et al.

[11] Patent Number: 5,608,169
[45] Date of Patent: Mar. 4, 1997

[54] DEVICE AND METHOD FOR TESTING THE BEARING CAPACITY OF PILES

[75] Inventors: Toyokazu Fujioka; Kunihiko Arai, both of Kanagawa-ken, Japan

[73] Assignee: Chiyoda Corporation, Japan

[21] Appl. No.: 492,309

[22] Filed: Jun. 19, 1995

[30] Foreign Application Priority Data

| Jul. 26, 1994 | [JP] | Japan | 6-192678 |
| Aug. 25, 1994 | [JP] | Japan | 6-222699 |
| Nov. 17, 1994 | [JP] | Japan | 6-307094 |
| Dec. 9, 1994 | [JP] | Japan | 6-331011 |

[51] Int. Cl.$^6$ .................................................. G01N 3/00
[52] U.S. Cl. .................................................. 73/803; 73/786
[58] Field of Search .................................................. 73/9, 84, 784, 73/786, 803

[56] References Cited

U.S. PATENT DOCUMENTS

| 3,894,588 | 7/1975 | Brill | 73/9 |
| 4,400,970 | 8/1983 | Ali | 73/84 |
| 4,614,110 | 9/1986 | Osterberg | 73/84 |
| 5,099,696 | 3/1992 | Yabuuchi | 73/784 |
| 5,127,270 | 7/1992 | Yabuuchi | 73/784 |

FOREIGN PATENT DOCUMENTS

| 48-27007 | 8/1973 | Japan . |
| 53-12723 | 5/1978 | Japan . |
| 6-63879 | 8/1994 | Japan . |

*Primary Examiner*—Richard Chilcot
*Assistant Examiner*—Ron Biegel

[57] ABSTRACT

A hydraulic jack assembly is interposed between at least a pair of adjacent sections of the pile, and a hollow center is defined in a central region of the hydraulic jack assembly, thereby allowing communication between adjacent sections of the pile. Thus, concrete can be filled into the shaft without creating any voids, in particular around the hydraulic jack assembly. Therefore, the integrity of the pile is not compromised by the presence of the hydraulic jack assembly, and the testing device in no way detracts from the performance of the pile. The hydraulic jack assembly may consist of an annular arrangement of individual hydraulic jacks or may consist of a single cylinder device defining an annular cylinder chamber between a pair of coaxial, mutually slidable cylinders. By placing a pile consisting of at least three sections in an earthen shaft, and interposing at least a pair of hydraulic jack assemblies each between an adjacent pair of the pile sections; it is possible to simultaneously actuate the pair of hydraulic jack assemblies so as to test the load supporting capacity of the pile section located between the hydraulic jack assemblies without being interfered by axial forces or displacements of other pile sections.

17 Claims, 20 Drawing Sheets

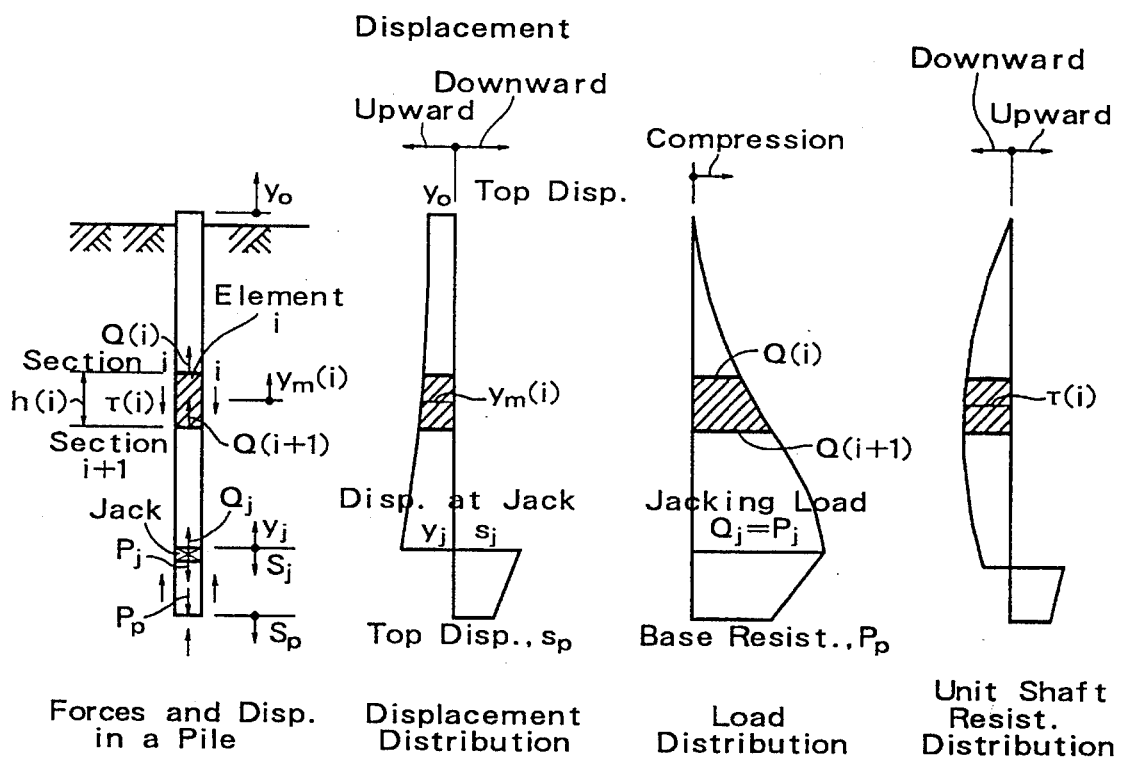
| Fig. 4(a) | Fig. 4(b) | Fig.4(c) | Fig.4(d) |
Forces and Disp. in a Pile / Displacement Distribution / Load Distribution / Unit Shaft Resist. Distribution
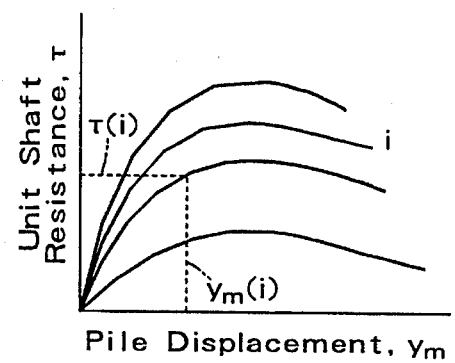
$\tau \sim y_m$ Curve
Fig. 4(e)
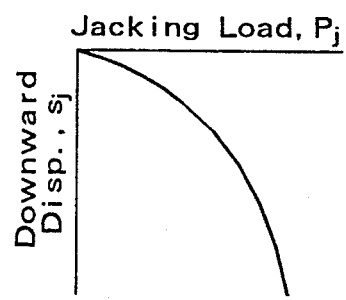
$P_j \sim s_j$ Curve
Fig. 4(f)

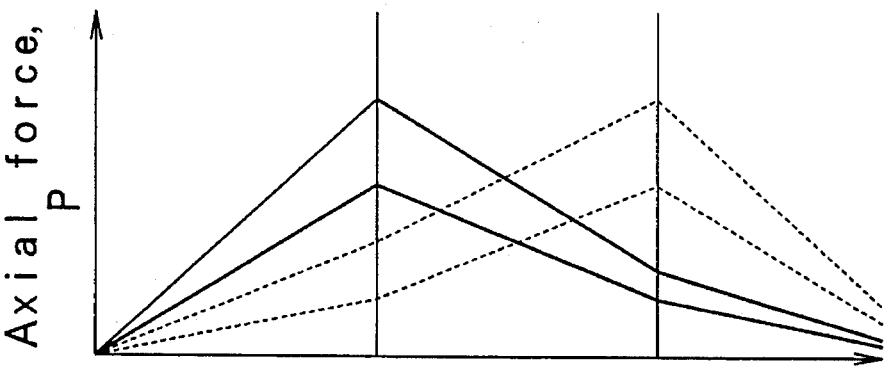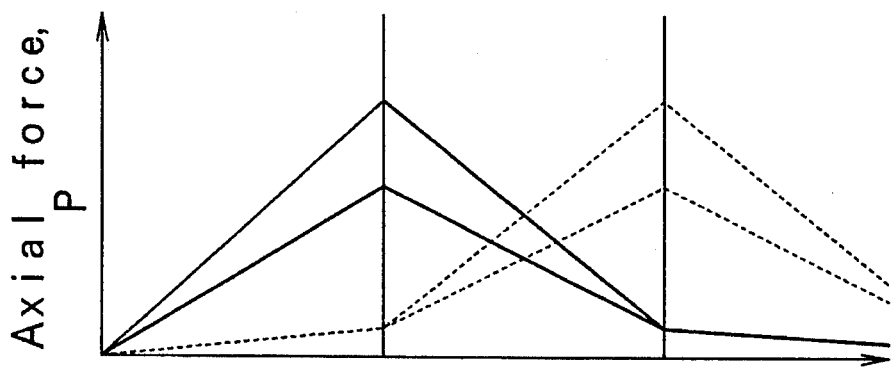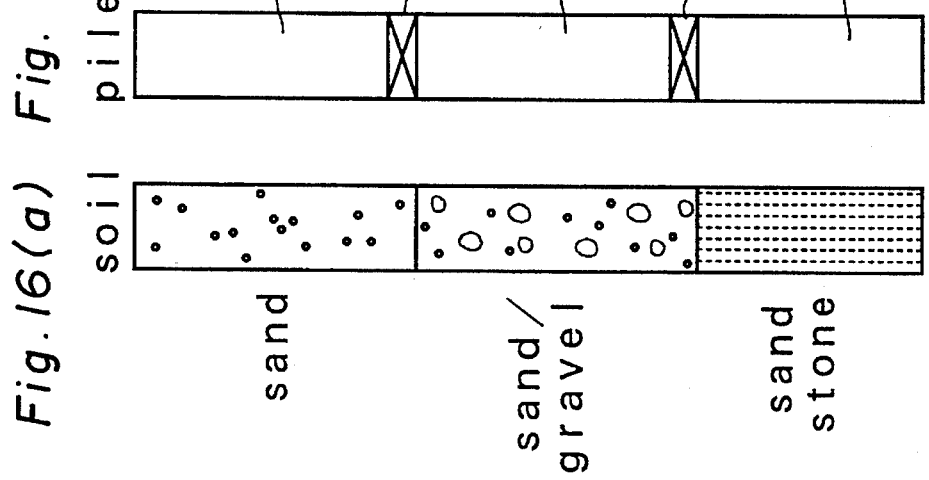

1

DEVICE AND METHOD FOR TESTING THE BEARING CAPACITY OF PILES

TECHNICAL FIELD

The present invention relates to devices and methods for measuring and otherwise testing the beating capacity of piles, and in particular to methods and devices for loading a pile made of concrete or other material, and driven into, placed in or cast in a shaft bored in the earth, and measuring the forces supporting the pile in the earthen shaft.

BACKGROUND OF THE INVENTION

The load supporting capacity of a concrete pile formed in an earthen shaft has been conventionally measured by placing a jack at the upper end of the pile, and supporting the reaction of the jack with earthen anchors and/or similar piles located around the concrete pile to be tested. The necessary downward load can be applied to the concrete pile by the jack, and the reaction acting on the jack can be supported by the resistance of the earthen anchors and/or the surrounding piles against the pulling force. To eliminate the need for the massive structure for supporting the reaction force produced by the jack, it was proposed to provide a hydraulic jack at the bottom end of the shaft, and supply hydraulic fluid from the ground surface. For instance, reference should be made to Japanese patent publication (kokoku) No. 48-27007 (Nakayama et al), Japanese patent publication (kokoku) No. 53-12723 (Sumii), and U.S. Pat. No. 4,614,110 issued Sep. 30, 1986 to Osterberg. By extending the hydraulic jack at the bottom of the shaft, it is possible to determine the end bearing capacity and the unit shaft resistance of the pile by measuring the displacements of the two ends of the hydraulic jack with respect to a fixed point of reference typically defined on the ground surface.

It was also proposed to provide a hydraulic jack in a middle part of the pile to more accurately evaluate the bearing capacity, in particular the unit shaft resistance of the pile. For instance, reference should be made to Japanese patent publication (kokoku) No. 6-63879 (Arai et al).

According to this previously proposed device, the hydraulic jack provided in an intermediate part of the pile creates a certain discontinuity. More specifically, because the central part of the hydraulic jack is closed, it is necessary to build the part of the pile below the hydraulic jack by first placing a steel cage for concrete reinforcement or a rebar cage in the bottom of the shaft, and placing concrete in this bottom region before installing the hydraulic jack. The same process is repeated for constructing the part of the pile above the hydraulic jack. In addition to the increase in the amount of work involved, it is difficult to prevent voids from being created immediately below the hydraulic jack. Furthermore, it is difficult to solidly connect the two parts of the rebar cage below and above the hydraulic jack with each other.

Also, this device is not applicable to bored precast piles which are staked into the ground as the earthen shafts are bored with an auger or other means.

BRIEF SUMMARY OF THE INVENTION

In view of such problems of the prior art, a primary object of the present invention is to provide a device for measuring the bearing capacity of a pile which can be installed at an arbitrary point of the pile without causing any undue difficulty in placement of concrete or in installment of the pile in the shaft.

A second object of the present invention is to provide a device for measuring the bearing capacity of a pile which allows the bearing capacity of the pile to be accurately measured even when the unit shaft resistance varies with depth.

A third object of the present invention is to provide a device for measuring the bearing capacity of a pile which can move the pile vertically without causing the pile to be deflected laterally even when the shaft and base resistances of the pile are not uniform around the pile.

A fourth object of the present invention is to provide a method for measuring the bearing capacity of a pile which allows arbitrary sections of the pile to be individually tested for accurate evaluation of the bearing capacity of the pile.

A fifth object of the present invention is to provide a method for measuring the bearing capacity of a pile which can apply a reciprocating load to a section of the pile.

According to the present invention, these and other objects can be accomplished by providing a device for measuring the bearing capacity of a pile placed in an earthen shaft, comprising: a hydraulic jack assembly interposed between at least a pair of adjacent sections of the pile; means for supplying hydraulic fluid to the hydraulic jack assembly; means for measuring displacements of an upper end and a lower end of the hydraulic jack assembly; and means for measuring an axial force acting on the pile; the hydraulic jack assembly defining a hollow center allowing communication between adjacent sections of the pile Because the center of the hydraulic jack assembly is hollow, concrete can be placed in the shaft without creating any voids, in particular around the hydraulic jack assembly. Therefore, the integrity of the pile is not compromised by the presence of the hydraulic jack assembly, and the testing device in no way detracts from the performance of the pile.

When the pile diameter is relatively large, the hydraulic jack assembly preferably comprises a plurality of individual hydraulic jacks arranged around and spaced from the axial center of the pile. The use of a number of relatively small hydraulic jacks is advantageous in terms of cost and reliability. To prevent the pile from deflecting laterally during the testing process due to the asymmetric supporting force of the soil surrounding the pile, flow regulating means may be provided for each of the hydraulic jacks to the end of uniformly lifting each of the hydraulic jacks.

Typically, the pile consists of a bored cast-in-place concrete pile reinforced by a rebar cage, and the hydraulic jack assembly is interposed between a pair of annular plates which are securely attached to an upper section and a lower section of the rebar cage, respectively. To prevent the hydraulic jack assembly from extending under the weight of the lower part of the pile or the rebar cage, the upper and lower annular plates or the separator plates attached to the annular plates may be connected with each other by tension rods which are adapted to be ruptured by the extension of the hydraulic jack assembly before testing.

It was discovered that each of the hydraulic jacks should be supported by one of the upper and lower annular plates by way of a spherical seat at least at one end thereof so as to accommodate slight deformation of the overall structure, slight deviation from purely axial loading and other unpredictable irregularities in the parameters during the process of testing.

Preferably, the upper and lower annular plates are provided with a pair of annular separator plates, and bellows are placed across inner and outer edges of the separator plates to keep concrete away from moveable parts of the hydraulic jack assembly. The gaps created by this structure are later filled by resin mortar or cement milk by way of conduits communicating these gaps to the ground surface. It is not desirable in the case of a bored cast-in-place pile to create any discontinuity in the rebar cage. For instance, longitudinal rebars may be secured to one of the annular plates and passed through openings provided in the other of the annular plates so that these longitudinal rebars may be effective as a part of the rebar cage. Again, to eliminate the possibility of creating any voids in the cast concrete, lower ends of conduits adapted to receive cement milk or resin mortar from the ground surface should be fitted on the rebars.

When the diameter of the pile is relatively small, the hydraulic jack assembly may comprise inner and outer cylinders having annular shoulder surfaces on mutually opposing sides thereof and being disposed in mutually slidable manner in a coaxial arrangement, thereby defining an annular cylinder chamber therebetween. In this case, the inner and outer cylinders may be engaged by shear or tension pins to prevent sagging of a lower end of the cylinder assembly under the weight of a section of the pile located under the hydraulic jack assembly.

Because the pile tends to be subjected to a twisting load when it is being staked into or otherwise introduced into the earthen shaft, to ensure the integrity of the sealing arrangement and other mechanical parts of the hydraulic cylinder assembly, the inner and outer cylinders may be engaged by radial pins passed through holes provided in one of the inner and outer cylinders, and received by notches provided in the other of the inner and outer cylinders, the notches opening toward a lower end of the associated cylinder so that the radial pins prevent relative rotation between the inner and outer cylinders in a retracted state of the hydraulic jack assembly without restricting extension of the hydraulic jack assembly.

Displacement of various parts of the pile and the hydraulic jack assembly can be conveniently and reliably measured by using a telltale rod having a lower end engaged by a part of the pile, and an upper end connected to a dial gage for measuring an axial movement of the telltale rod relative to a fixed point of reference.

Conventionally, it has not been possible to test a middle section of a pile even though it is known that the unit shaft resistance of a pile can significantly change with depth. However, according to the present invention, a pile consisting of at least three sections is placed in an earthen shaft with at least a pair of hydraulic jack assemblies each interposed between an adjacent pair of the pile sections; and the pair of hydraulic jack assemblies are actuated simultaneously or in synchronism to test a load supporting capacity of a desired one of the pile sections without being interfered with by axial forces or displacements of other pile sections. Also, it has not been conventionally possible to measure the bearing capacity of a pile in a comprehensive manner because at least one section of the pile must be kept immobile for the purpose of supporting the hydraulic jack assembly against the reaction force thereof, and the bearing capacity of this section therefore cannot be tested. The present invention allows each and every section of the pile to be tested by appropriately and selectively actuating the hydraulic cylinder assemblies.

Also, conventional methods were not capable of applying a reciprocating load to a pile section because the hydraulic jack assemblies normally consist of single acting cylinders which are capable of extending but incapable of retracting in a positive sense. The present invention allows a reciprocating load to be applied to a pile section in a similar structure by alternatingly actuating the pair of hydraulic jack assemblies to apply a reciprocating load to one of the pile sections located between the hydraulic jack assemblies. This is highly advantageous in evaluating the performance of the pile which is subjected to a load caused by an earthquake or wind.

BRIEF DESCRIPTION OF THE DRAWINGS

The present invention is described as follows, with reference to the appended drawings, in which:

FIG. 4 includes diagrams and graphs showing typical relationships between displacements, loads, and unit shaft resistance distributions in a pile;

FIG. 16 includes various diagrams for showing the load distributions along a pile;

DETAILED DESCRIPTION OF THE PREFERRED EMBODIMENTS

Figure 1:
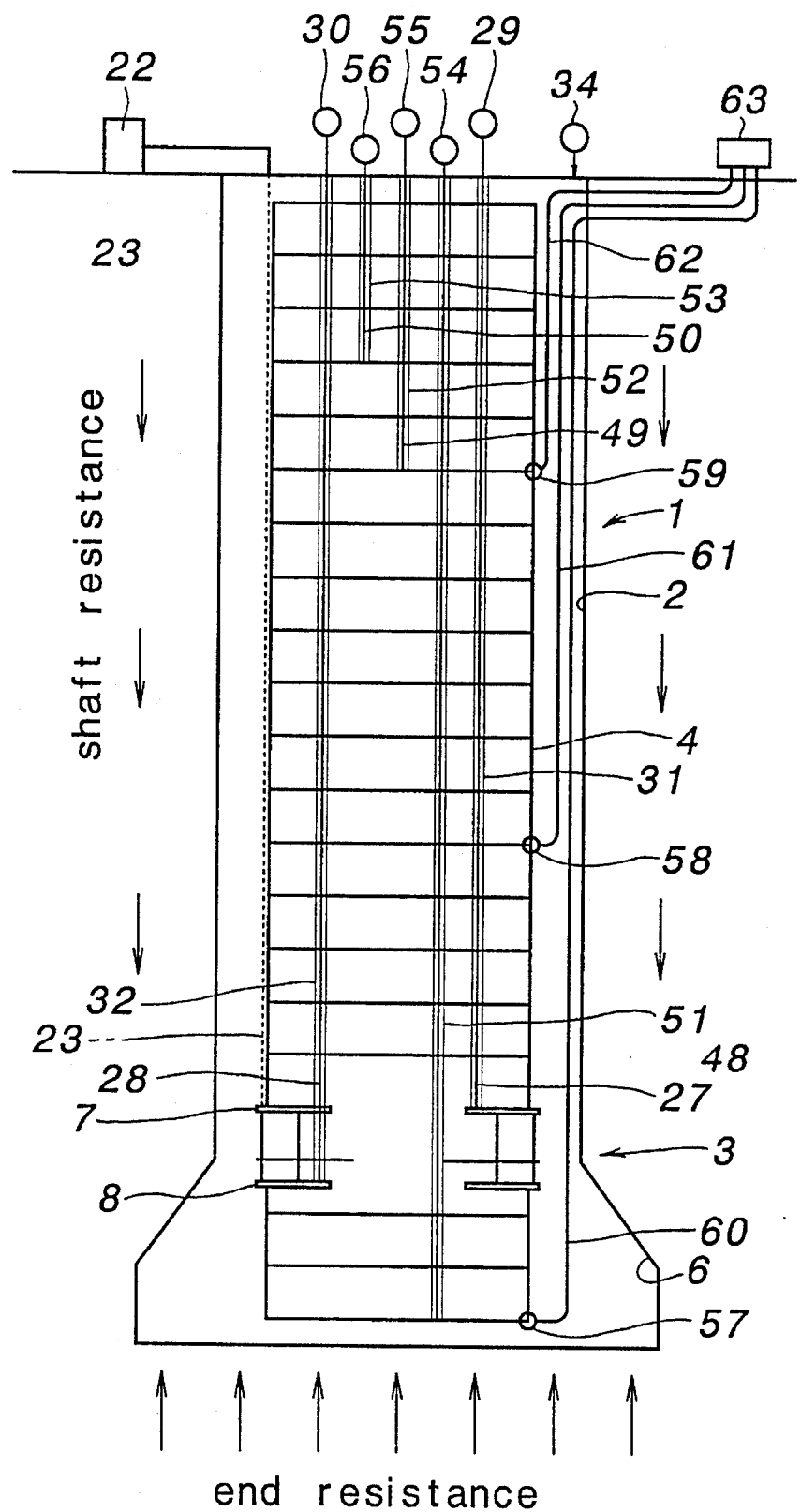
FIG. 1 is a sectional side view of a first embodiment of the present invention applied to a bored cast-in-place concrete pile.
Figure 2:
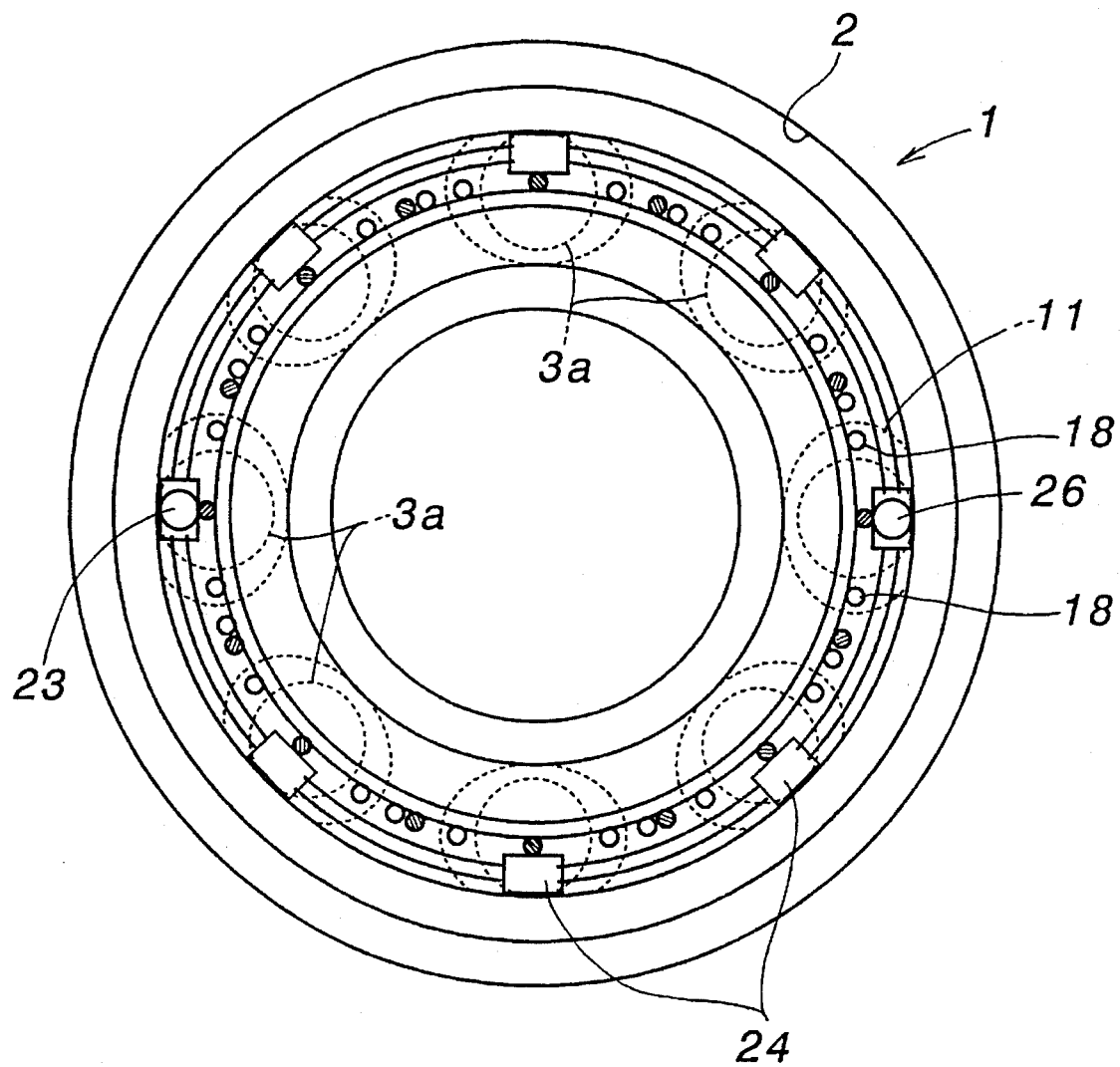
FIG. 2 is a sectional view taken along line II—II of FIG. 1.
Figure 3:
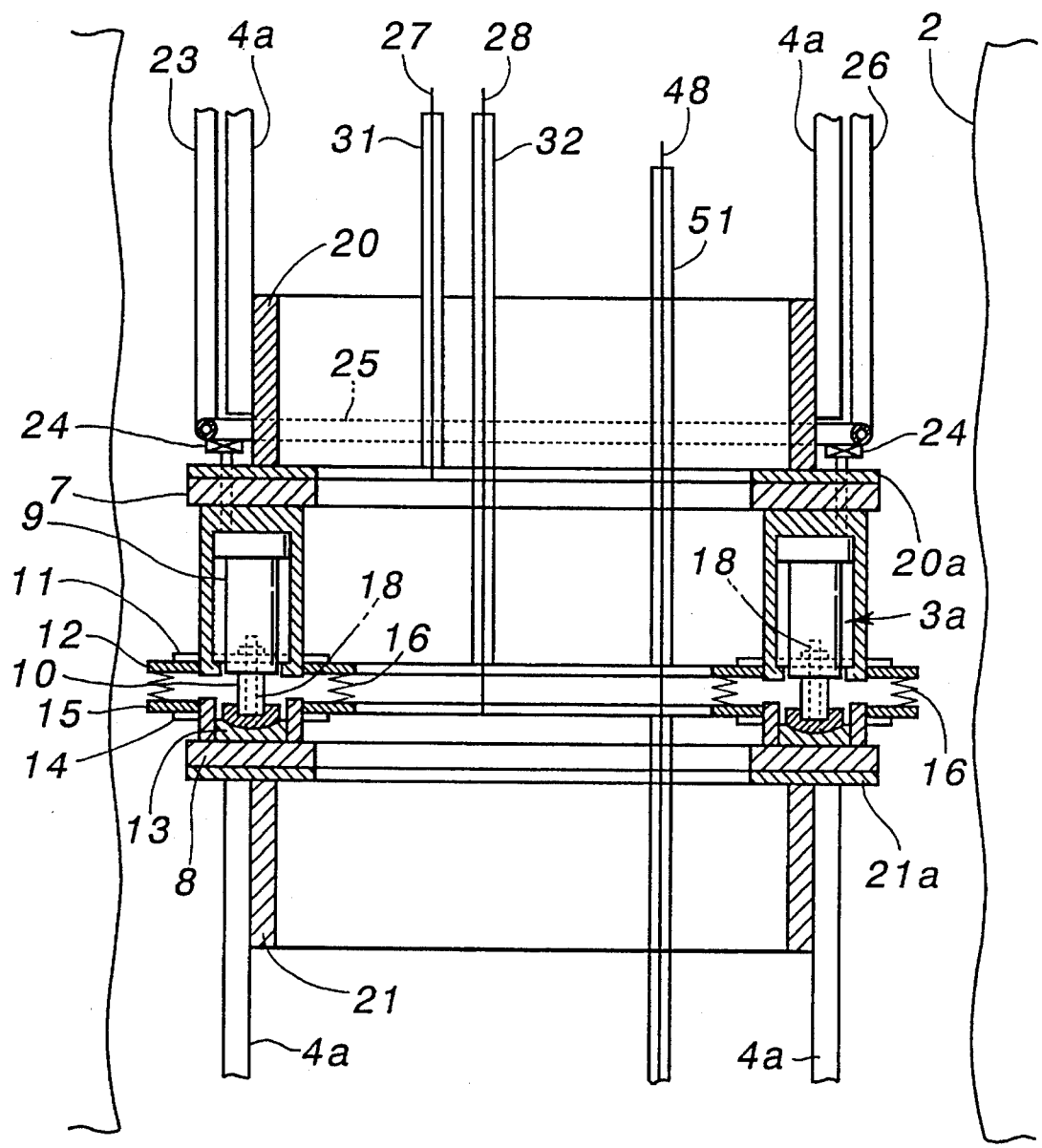
FIG. 3 is an enlarged sectional view showing a part of FIG. 1.

FIGS. 1 through 3 show a first embodiment of the present invention. An earthen shaft 2 is drilled to a desired depth and with a desired diameter. A hydraulic jack assembly 3 which is described in more detail hereinafter is provided in an intermediate part of a cylindrical rebar cage 4, and this rebar cage 4 along with the hydraulic jack assembly 3 is lowered into the shaft 2. Then, concrete is poured into the shaft 2 by using a tremie not shown in the drawings.

In this embodiment, the hydraulic jack assembly 3 consists of a plurality of individual hydraulic jacks 3a arranged in an annular fashion, and is placed slightly above the underreamed portion 6 of the shaft 2 formed at the bottom end thereof. The hydraulic jacks 3a are interposed between a pair of annular plates 7 and 8 which are disposed coaxially with the center of the shaft 2.

As best shown in FIG. 3, each of the hydraulic jacks 3a comprises a cylinder 9 attached to the lower surface of the upper annular plate 7, and a ram 10 slidably received in the cylinder 9. An annular separator plate 12 is attached to the lower ends of the cylinders 9 via flanges 11 formed at the lower ends of the cylinders 9. The upper surface of the lower annular plate 8 is provided with a plurality of spherical seats 13, and another annular separator plate 15 is attached to the upper ends of the spherical seats 13 via flanges 14 formed at the upper ends of the spherical seats 13. A pair of annular bellows 16 are attached across the upper and lower separator plates 12 and 15 along both internal and external edges thereof.

Each of the spherical seats 13 supports the lower end of an associated one of the rams 10. Each associated pair of the flanges 11 and 14 are joined by a pair of steel tension rods 18 to keep the upper and lower parts of the rebar cage 4 joined together. These tension rods 18 are each provided with a notch so that the tension rods 18 may rupture when they are slightly elongated with a relatively small force.

As a means for securely attaching the rebar cage 4 to the hydraulic jack assembly 3, a steel pipe 20 having a flange 20a may be secured to the upper surface of the upper annular plate 7 so that the lower ends of the longitudinal rebars 4a in the upper part of the rebar cage 4 may be welded or otherwise secured to this steel pipe 20, and another steel pipe 21 having a flange 21a may be secured to the lower surface of the lower annular plate 8 so that the upper ends of the longitudinal rebars 4a in the lower part of the rebar cage 4 may be welded to this steel pipe 21. Alternatively, the opposing ends of the longitudinal rebars 4a may be welded, screwed or otherwise secured to flanges 20a and 21a, and secure these flanges 20a and 21a to the upper and lower annular plates 7 and 8, respectively.

Hydraulic fluid is supplied to the individual hydraulic jacks 3a by a pressure pump 22 placed on the ground surface via a supply hose 23. Each of the inlet ports leading to the cylinders 9 is provided with a flow rate regulator 24 which ensures an identical volume of the hydraulic fluid is introduced into each of the cylinders 9, and is connected to a common communication conduit 25 extending annularly along the cylinders 9. The lower end of the supply hose 23 is connected to the annular communication conduit 25. An air purge hose 26 is also connected to this annular communication conduit 25 diagonally opposite to the supply hose 23, and extends upward to the ground surface. The supply hose 23 in this embodiment consists of a single hose, but may also consist of a plurality of parallel hoses. The same is true with the air purge hose 26.

Telltale rods 27 and 28 are secured to the upper and lower annular plates 7 and 8, respectively, and extend to the ground surface where they are connected to dial gages 29 and 30, respectively. Also, similar telltale rods 48, 49 and 50 are attached to suitable parts of the rebar cage 4, and extend to the ground surface where they are connected to dial gages 54, 55 and 56, respectively. Additionally, strain gages 57, 58 and 59 are attached to suitable locations of the pile 1 or the rebar cage 4, and lead wires 60, 61 and 62 extend to the ground surface where they are connected to a strain indicator 63 so that the axial force acting on the pile and the displacement of the pile may be measured at desired points. The telltale rods are kept from the surrounding concrete by tubular sheaths 31, 32, 51, 52 and 53. Thus, it is possible to measure the movements of the upper and lower annular plates 7 and 8 with respect to a fixed reference placed on the ground surface. Numeral 34 in FIG. 1 denotes a dial gage for detecting the displacement of the top end of the pile 1.

The mode of installing the above described pile assembly is described as follows.

First of all, the hydraulic jack assembly is placed in an intermediate point of a rebar cage 4 on the ground surface. The longitudinal rebars 4a of the rebar cage 4 are welded to the steel pipes 20 and 21 attached to the upper and lower annular plates 7 and 8, respectively, of the hydraulic jack assembly 3. The lower ends of the telltale rods 27, 28, 48, 49 and 50 are attached to the upper and lower annular plates 7 and 8, and the suitable parts of the rebar cage 4, and are fitted with the protective sheaths 31, 32, 51, 52 and 53. The strain gages 57, 58 and 59 are also attached to suitable locations of the longitudinal rebars 4a of the rebar cage 4, and the lead wires 60, 61 and 62 therefor are passed upward to the strain indicator 63 along the longitudinal rebar 4a of the rebar cage 4. The entire assembly is then lowered into the shaft 2. If the entire length of the pile 1 is large, each additional section of the rebar cage 4 may be added as the cage assembly is lowered into the shaft 2. In the latter case, the telltale rods are also extended by adding new section of the telltale rods as new sections are added to the rebar cage 4. When the entire rebar cage 4 is lowered into the shaft 2, concrete is poured into the shaft via a tremie not shown in the drawings.

Thus, the hydraulic jack assembly 3 can be installed at any point of the rebar cage 4 via the upper and lower annular plates 7 and 8. Because the separator plates 12 and 15 as well as the upper and lower annular plates 7 and 8 are all annular, and jointly define a hollow central passage, it is possible to lower the tremie all the way down into the shaft, and pour concrete in the conventional manner without any substantial modification. Because the bellows 16 extend across both the inner and outer peripheral edges of the pair of separator plates 12 and 15, cement or other foreign matters are prevented from getting into the cylinders 9, the spherical seats 13, and the protective sheaths 31 and 32.

After the concrete has been cured for a certain number of days, hydraulic fluid under pressure is fed into the supply hose 23 while air trapped in the jacks 3a is purged from the air purge hose 26. When the air is thoroughly purged, the outer opening of the air purge hose 26 is closed. As more hydraulic fluid is pumped into the jacks 3a, eventually the part of the concrete filled around the bellows 16 between the two separator plates 12 and 15 is ruptured due to the tensile force acting on it, and this causes a sharp decline in the hydraulic pressure, and allows slight extension of the rams 10 at the same time. The rupture of this part of the concrete can be detected either by the sharp decline of the hydraulic pressure or by the displacements of the telltale rods which are detected by the dial gages.

Thereafter, the hydraulic jacks are further pressurized, and the resulting displacements and strains of the various parts of the pile 1 can be measured. Thus, the bearing capacity of the pile 1 can be tested by applying a mutually opposing axial force with the jack assembly placed at an arbitrary point of the pile 1.

FIG. 4 schematically illustrates data that can be obtained by this process of evaluating the bearing capacity of a pile. FIGS. 4(a) through (d) include typical curves showing displacement, load, and unit shaft resistance in a pile. This pile is divided into n elements each having the length of h(i) where "i" indicates a position on the pile, and i=1, . . . , n. Other variables are summarized in the following:

P and Q: axial forces

τ: unit shaft resistance acting on the associated element y and S: axial displacement A family of unit shaft resistance-displacement relations are shown in FIG. 4(e). FIG. 4(f) shows the relationship between the axial force acting on the lower end of the jack assembly and the displacement at this point. The measured values of strain are converted into axial forces by using the elastic modulus and the cross sectional area of the pile, and the slope of the load distribution curve at any depth, divided by the perimeter length, yields the unit shaft resistance at the depth. Base on the relationship expressed by the graphs of FIG. 4(e) and 4(f), it is possible to transform the results into equivalent load-settlement relationships of the pile axially loaded at the head by using load transfer analysis.

After the test has been completed, the outer opening of the air purge hose 26 is opened, and hydraulic fluid is replaced by cement milk, resin mortar or other fluid that will harden in time by pumping it into the supply hose 23. At the same time, cement milk or an equivalent thereof is poured into the protective sheaths as well, and will eventually fill up all the voids inside the jack assembly 3 including the gaps in the concrete which are created between the separator plates 12 and 15. Once the gaps and voids are thus filled by cement or other material, the pile can be used as a normal pile.

Figure 3A:
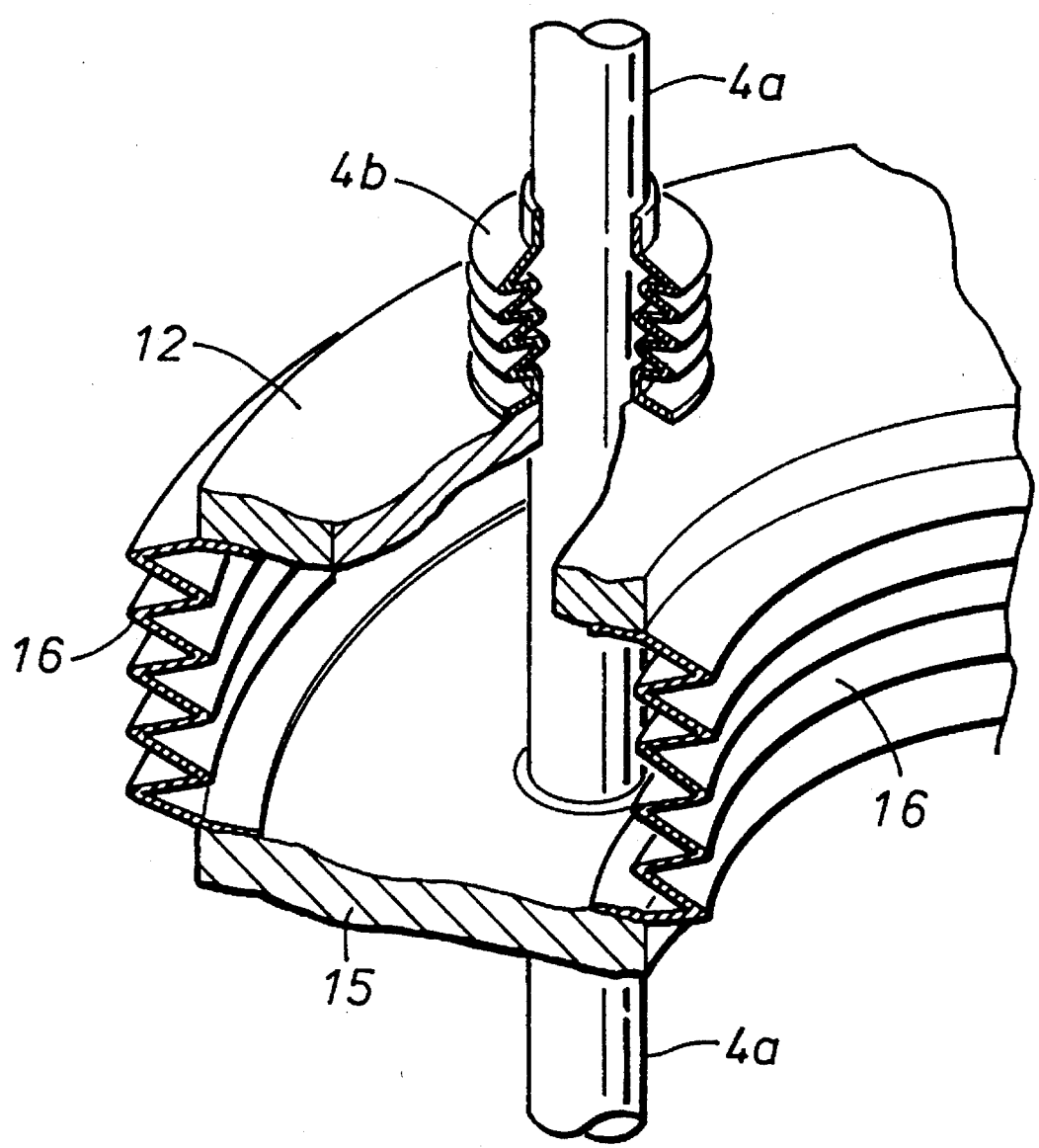
FIG. 3a is a fragmentary sectional view of a part of the hydraulic jack assembly including rebars passed through one of the separator plates.

To reinforce the part of the concrete pile 1 adjacent to the hydraulic jack assembly 3, the rebar cage 4 may be adapted so as to minimize a discontinuity thereof due to the presence of the hydraulic jack assembly 3. In the modified embodiment illustrated in FIG. 3a, a plurality of rebars 4a are welded to the upper surface of the lower separator plate 15, and passed upward through associated holes provided in the upper separator plate 12. These rebars 4a are covered by protective sheaths 4b to keep off cement during the process of casting the pile prior to the process of testing. The longitudinal rebars of the lower cage 4 is welded to the lower surface of the lower separator plate 15. When the process of testing has been completed, cement milk is filled into the gaps between the sheaths and the rebars. If desired, the protective sheaths for the rebars may be joined together so that a fewer number of hoses have to be extended to the ground surface. Some of these hoses may be used as air purge hoses while the remaining hoses may be used as supply hoses for cement milk. Thus, these rebars will be effective in reinforcing the concrete, and the part of the pile adjacent to the hydraulic jack assembly can be made mechanically as strong as the remaining part of the pile. It is also possible to use rebars which are welded to the upper separator plate 12, and extend them downward through the lower separator plate 15.

Although the pile 1 or the shaft 2 in the above described embodiment had an expanded bottom end, the present invention is equally applicable to cylindrical piles. Also, the present invention can be applied to piles having various other cross sectional shapes, including rectangular and elliptic piles.

Figure 5:
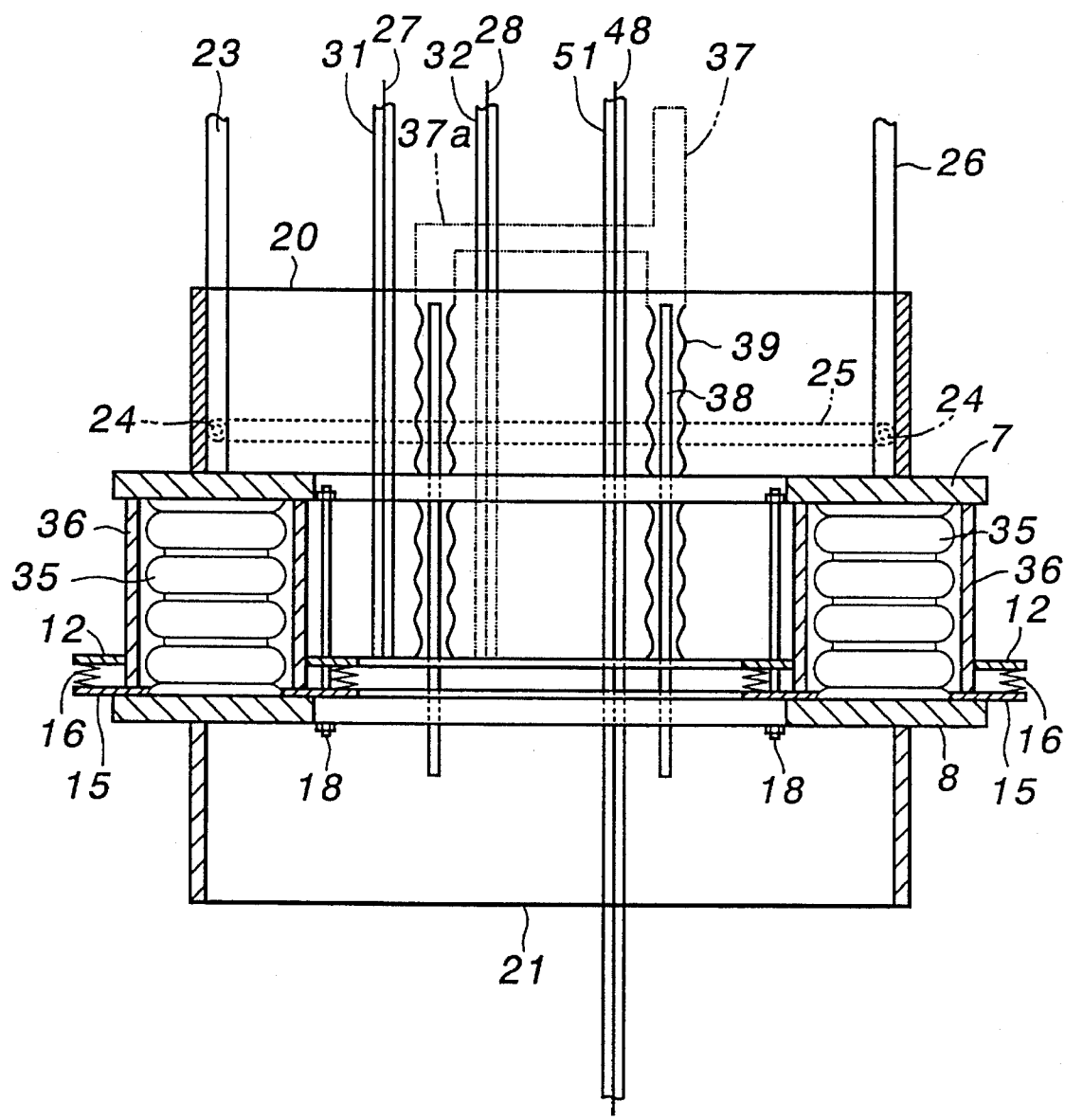
FIG. 5 is a view similar to FIG. 3 showing a second embodiment of the present invention.

FIG. 5 shows a second embodiment of the present invention which uses bellows instead of the cylinder and ram arrangement as individual elements for the hydraulic jack assembly 3. In this embodiment, the parts corresponding to those of the previous embodiments are denoted with like numerals. A plurality of bellows 35 are interposed between the upper and lower annular plates 7 and 8. Each of the bellows 35 is surrounded by a steel tube 36 having one end securely welded to the lower surface of the upper annular plate 7, and the other end abutting the upper surface of the lower annular plate 8. An annular separator plate 12 is secured to parts of the steel tubes 36 near the lower end thereof, and a similar separator plate 15 is fixedly secured to the upper surface of the lower annular plate 8. The upper and lower annular plates 7 and 8 are connected with each other by a plurality of tension rods 18. Longitudinal rebars 38 belonging to the upper section of the rebar cage 4 are attached to the lower annular plate 7 and passed through the openings provided in the upper annular plate 8 and the upper separator plate 12. Each of the rebars 38 are covered by a protective sheath 39 which is connected to a common communication conduit 37a. Longitudinal rebars belonging to the lower section of the rebar cage 4 are attached to the lower annular plate 8 or the lower separator plate 15. Numeral 37 denotes grout tubes which extend to the ground surface to feed cement milk into the gaps between the rebars 38 and the protective sheaths 39 via the communication conduit 37a.

Figure 6:
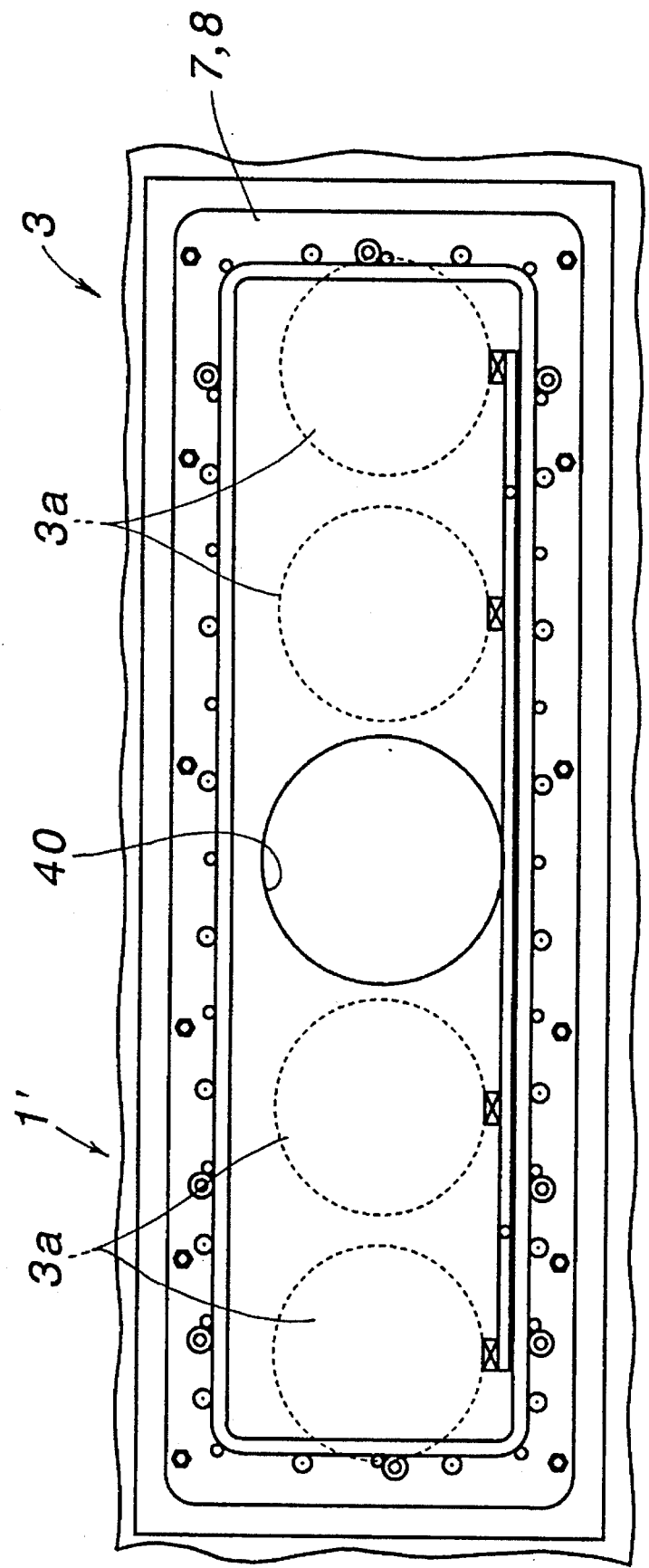
FIG. 6 is a sectional view similar to FIG. 2 showing a third embodiment of the present invention.

FIG. 6 shows a third embodiment of the present invention which is applied to a diaphragm wall or slurry wall 1'. Again, the parts corresponding to those of the previous embodiments are denoted with like numerals. In this embodiment, the hydraulic jack assembly comprises four hydraulic jacks 3a arranged in a single row, and is interposed between a pair of rectangular plates 7 and 8. The upper and lower rectangular plates 7 and 8 are each provided with a central opening at a mutually aligned position defining a bore 40 which vertically runs through the hydraulic jack assembly.

Figure 7:
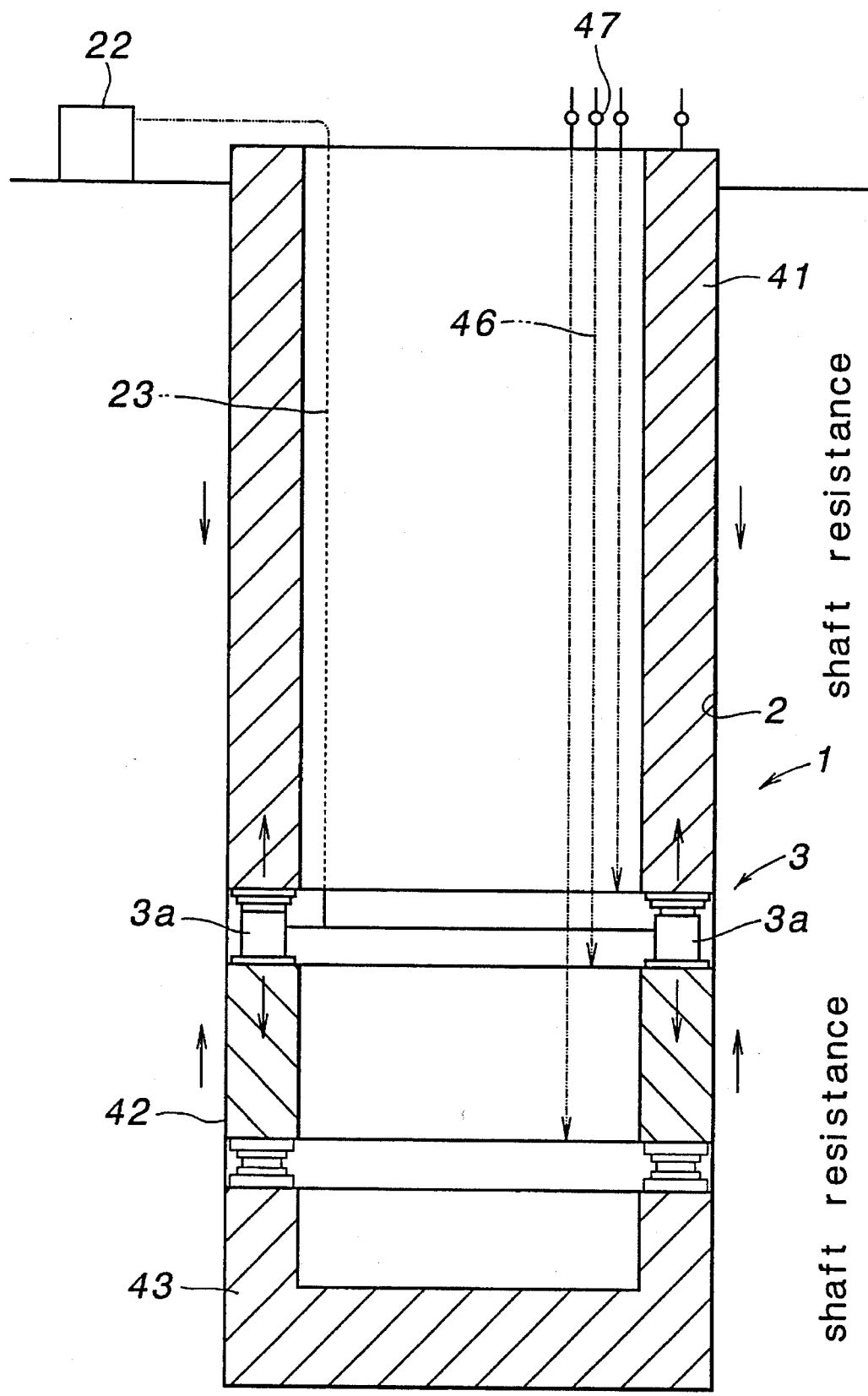
FIG. 7 is a sectional side view showing a fourth embodiment of the present invention applied to a bored precast concrete pile.
Figure 8:
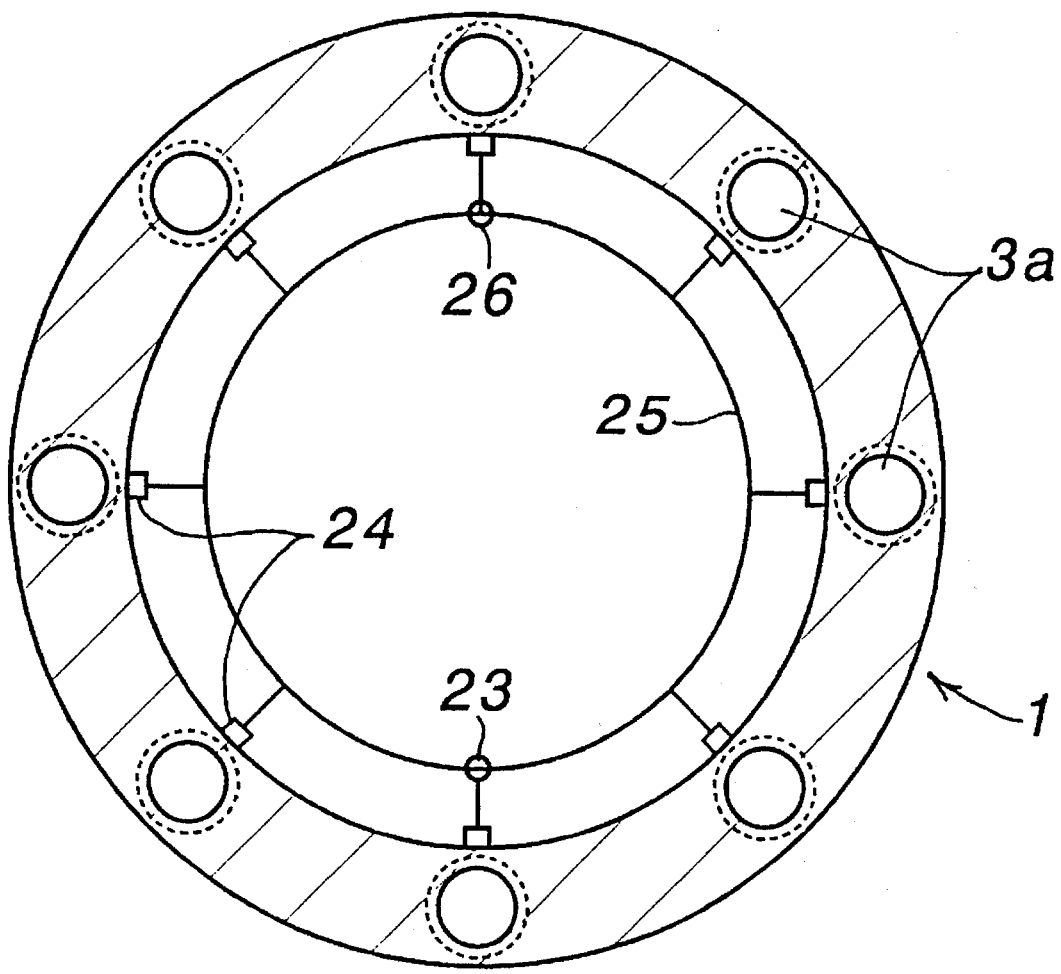
FIG. 8 is a sectional view taken along line VIII—VIII of FIG. 7.
Figure 9:
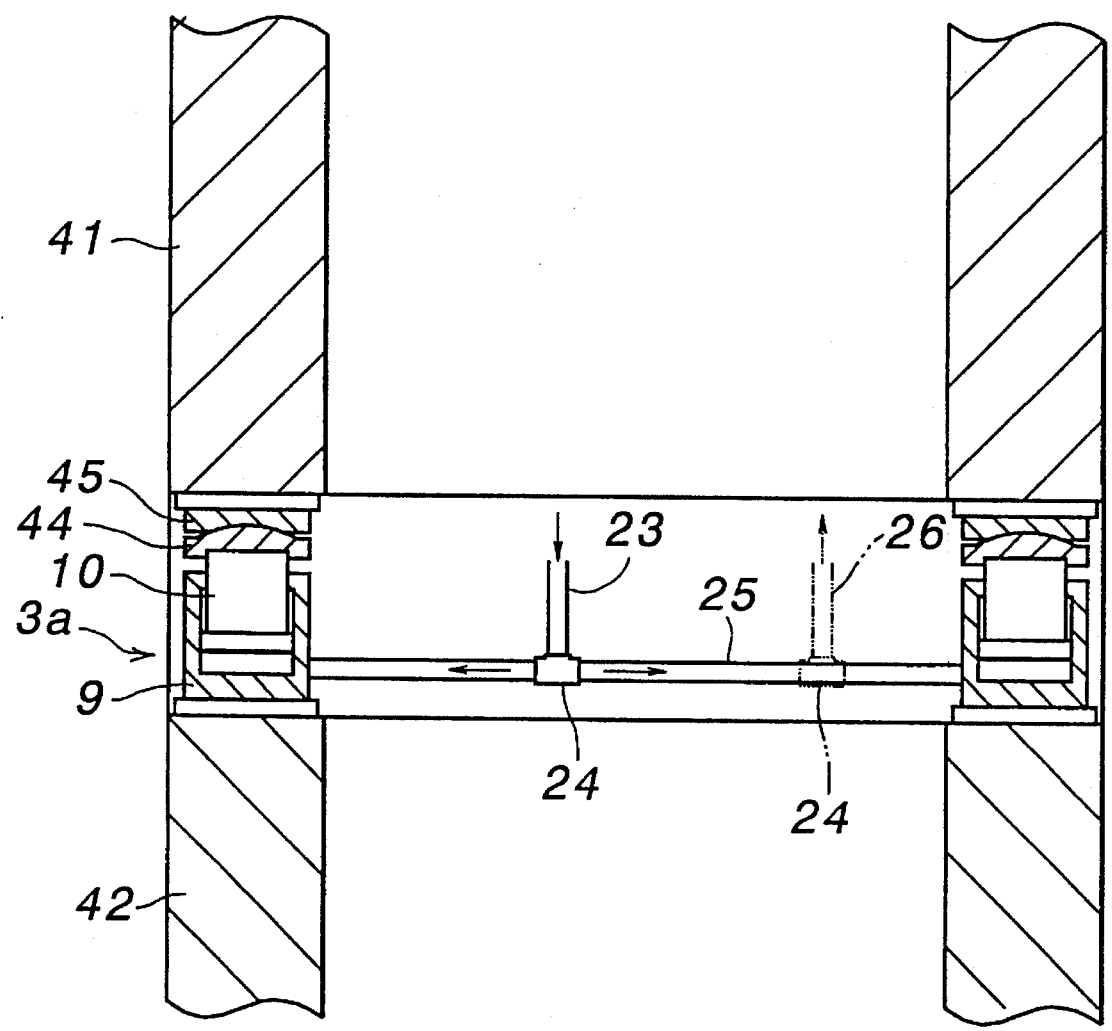
FIG. 9 is an enlarged sectional view showing a part of FIG. 7.

FIGS. 7 through 9 show a fourth embodiment of the present invention which is applied to a hollow cylindrical pile 1 which is placed in an earthen shaft. This pile 1 consists of three sections 41, 42 and 43 arranged along the length of the shaft 2, and a hydraulic jack assembly 3 comprising a plurality of hydraulic jacks 3a is interposed at least between two adjacent sections of the pile 1. For instance, a plurality of cylinders 9 are placed on the upper end of the middle section 42 of the pile, and rams 10 are slidably received in these cylinders 9. The upper ends of the rams 10 are formed as spherical shoes 44 which are supported by complementary spherical seats 45 secured to the lower end of the upper section 41 of the pile 1. The inlet ports of the cylinders 9 are provided with flow rate regulators 24, and are connected to a common communication conduit 25 extending concentrically around the center of the pile 1. A feed hose 23 and an air purge hose 26 are connected to this communication conduit 25, and extend to the ground surface. Numeral 46 denotes a telltale rod, and numeral 47 denotes a dial gage, both for indicating the displacement of the middle section 42 of the pile 1.

The pile 1 of this embodiment is a concrete pile consisting of plurality of sections. By appropriately arranging the length of each section, it is possible to measure the end resistance and the unit shaft resistance. More specifically, the pressurization of the hydraulic jack assembly 3 causes the adjacent sections to be pushed apart, and the unit shaft resistance (and/or the end resistance) of one of the sections can be tested by supporting the reaction acting on the hydraulic jack assembly by the unit shaft resistance (and/or the end resistance) of the adjacent section. Again, by virtue of the flow regulating valves 24, the movement of the different sections of the pile is guided along the axial length thereof, and the lateral deflection of the pile can be effectively prevented even when the unit shaft resistance is not uniform along the circumference of the pile 1.

FIGS. 10 to 14 show a fifth embodiment of the present invention applied to a precast pile adapted to be placed in an earthen shaft. In this embodiment, a hydraulic jack assembly 3 is incorporated in an intermediate part of a precast pile 1. The pile 1 is generally cylindrical in shape and defines an inner bore 51. The hydraulic jack assembly 3 comprises a hollow outer cylinder 52, and an inner hollow cylinder 53 slidably received in the outer cylinder 52. The inner cylinder 53 is provided with an downwardly facing annular shoulder 54 on its outer circumferential surface while the outer cylinder 52 is provided with a upwardly facing annular shoulder 55 on its inner circumferential surface so that an annular chamber 56 may be defined between them. O-rings 57 and 58 are interposed in the interface between the two cylinders to achieve an effective seal of the annular cylinder chamber 56. Thus, by introducing hydraulic fluid under pressure into the annular cylinder chamber 56, the two cylinders 52 and 53 can be moved away from each other. The upper end of the inner cylinder 53 is provided with a radial flange 59 which abuts the upper end of the outer cylinder 52 when the cylinder chamber 56 is not pressurized.

Figure 14:
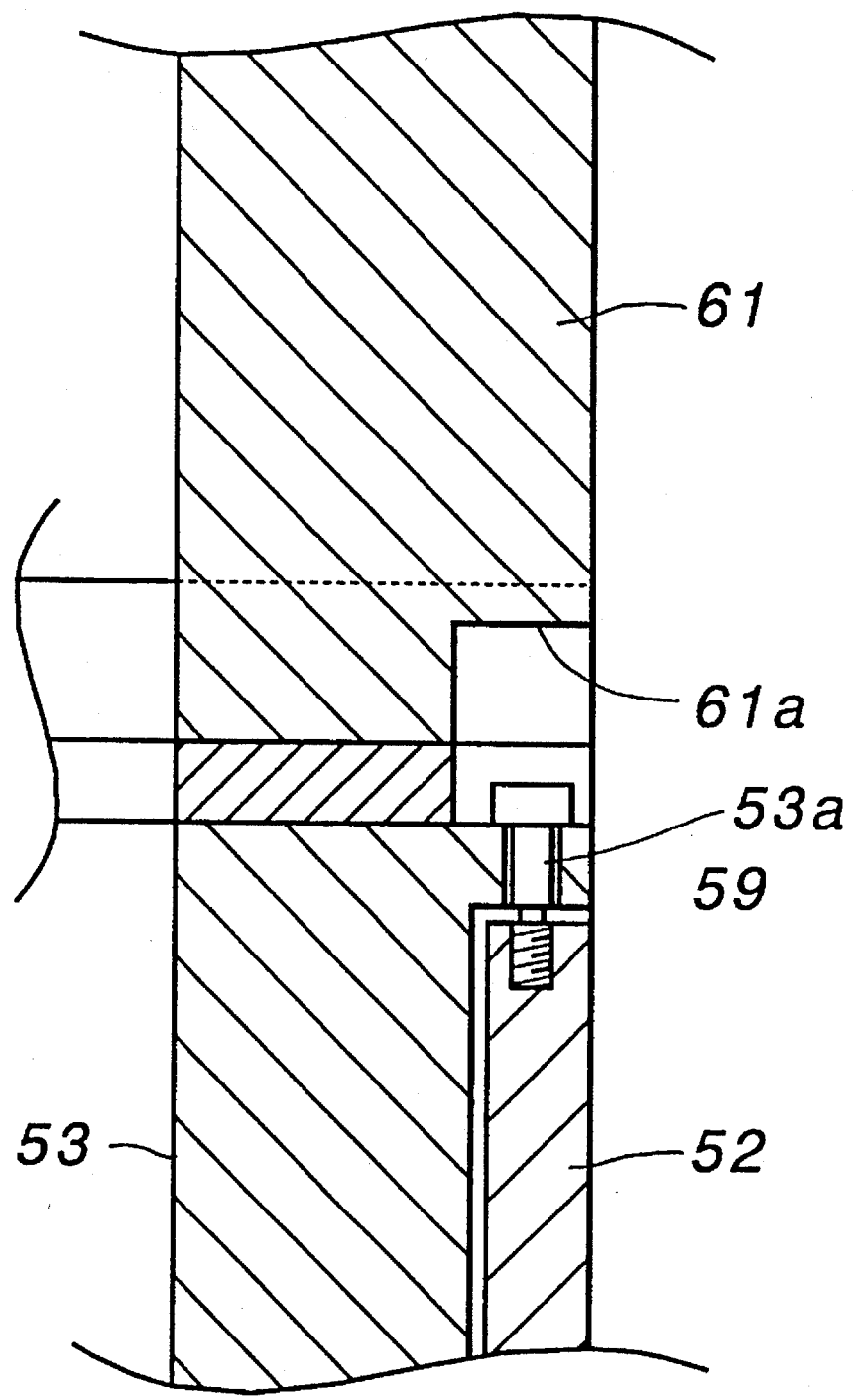
FIG. 14 is a fragmentary sectional view showing a modification of the fifth embodiment.

This embodiment can be conveniently applied to a precast pile which is placed in a bored or drilled earthen shaft. The hydraulic jack assembly 3 is placed between two sections 61 and 62 of the precast pile 1. To prevent the outer cylinder 52 from sagging under the weight of the lower section 62 of the pile 1, shear bolts 63 are passed through the walls of the inner and outer cylinders 52 and 53. Alternatively, tension bolts 53a may be passed through the flange 59 provided at the upper end of the inner cylinder 53 and threaded into the upper end of the outer cylinder 52 as illustrated in FIG. 14. The heads of the tension bolts 53a are received in recesses 61a provided in the lower end of the upper section 61 of the pile 1. These shear bolts 63 and tension bolts 63a are provided with notches so that they may rupture when the upper and lower cylinders 52 and 53 are extended away from each other, and a relatively small shear force or a relatively small tension is applied to them.

The lower end of the inner cylinder 53 is provided with a plurality of notches 64 and stop bolts which are passed through holes provided in the outer cylinder 52, and are received in the notches 64 so that the inner cylinder 53 and the outer cylinder 52 may not rotate relative to each other when the pile 1 is being forced into the earthen shaft 2 in its retracted state and it may be rotated around its axial center line. These stop bolts 65 prevent the shear bolts 63 from rupturing due to the torque which may develop between the inner and the outer cylinders 52 and 53 when the pile 1 is being placed in the shaft 2, but would not prevent the upper and lower cylinders 52 and 53 from extending away from each other.

Figure 12:
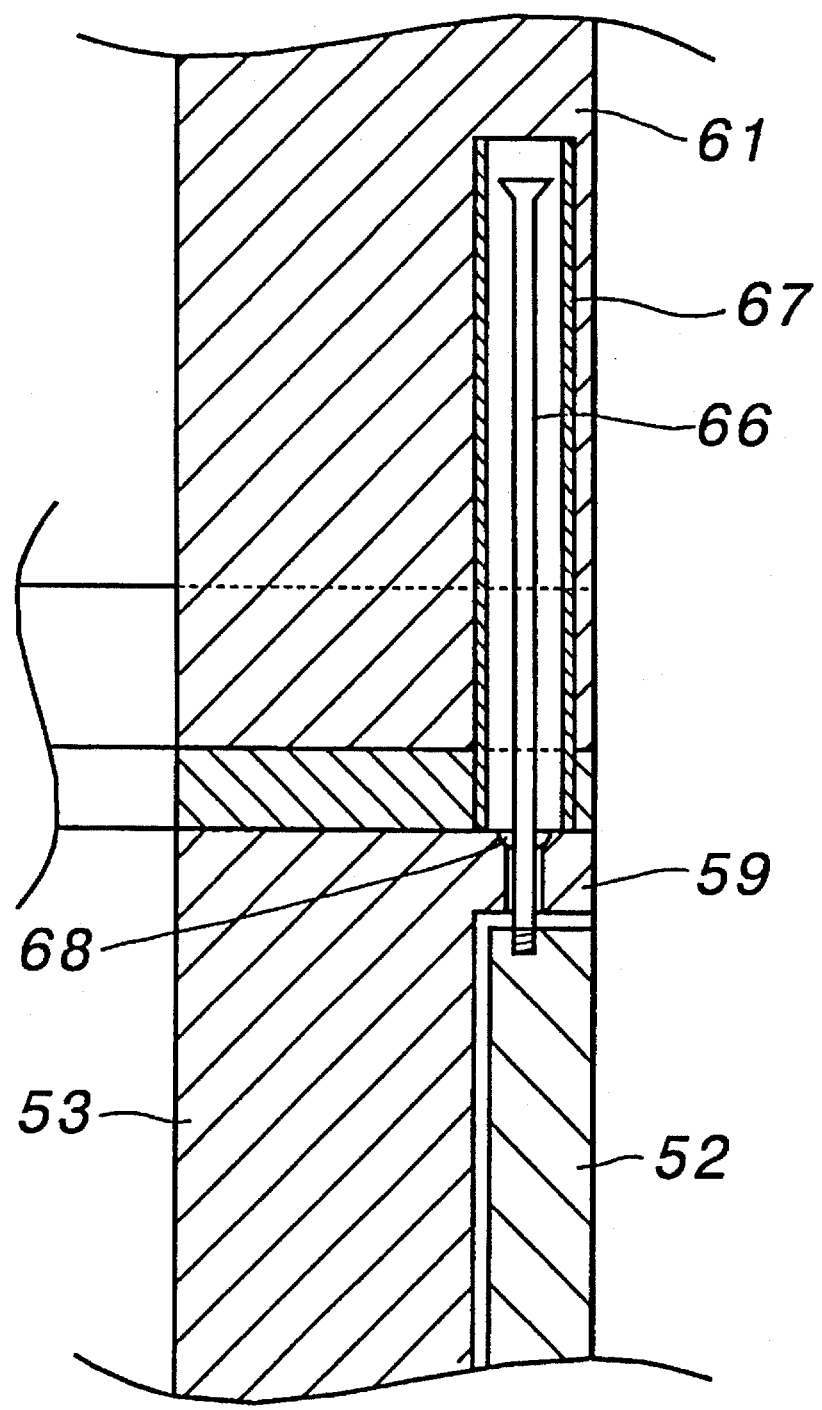
FIG. 12 is an enlarged fragmentary sectional view showing a part of the pile of FIG. 10.
Figure 13:
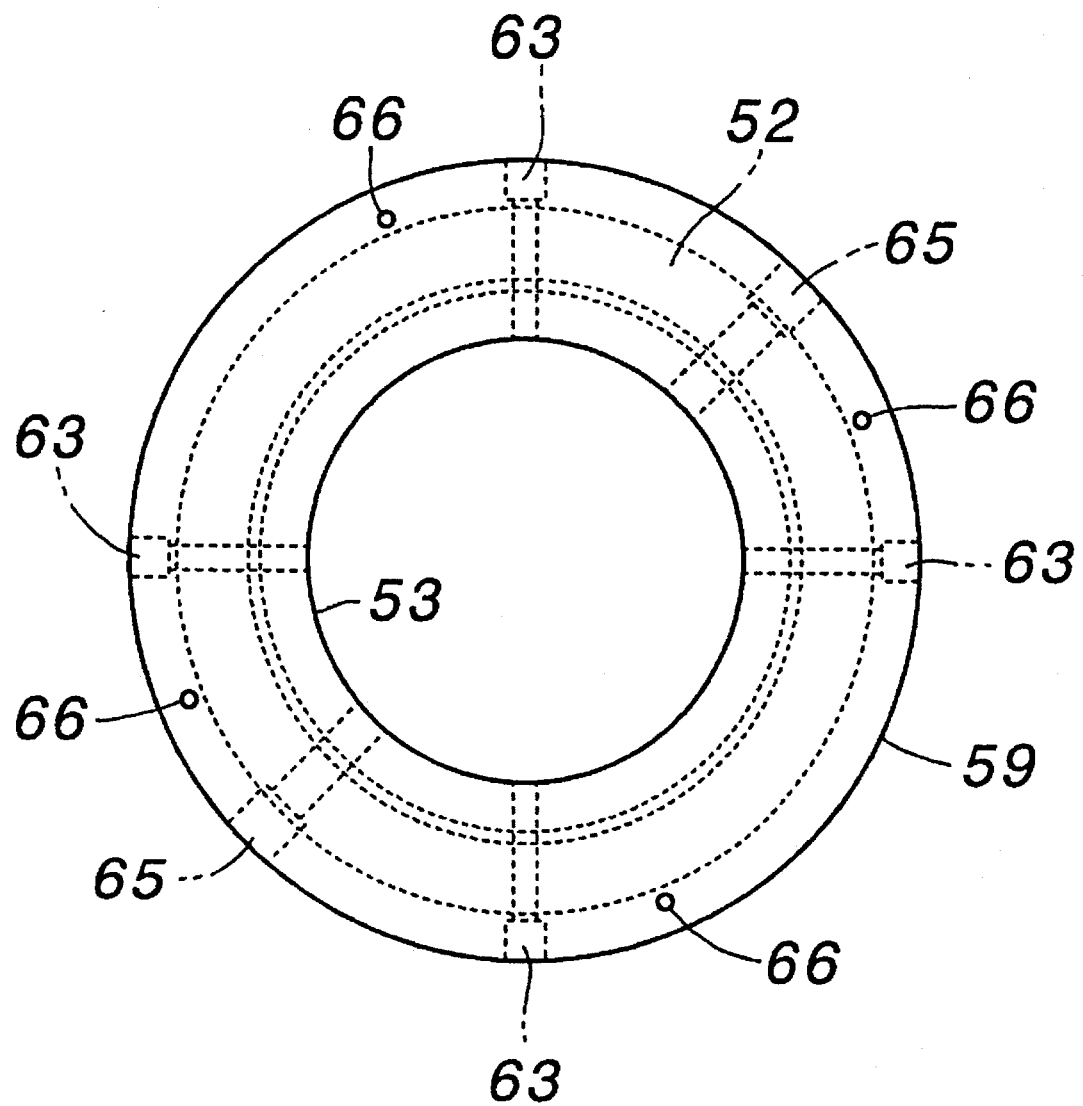
FIG. 13 is a top view of the hydraulic jack assembly of FIG. 10.

As best illustrated in FIG. 12, a plurality of stopper rods 66 are passed through the flange 59 at the upper end of the inner cylinder 53, and the lower ends of the stopper rods 66 are received in associated holes provided in the upper end of the outer cylinder 52 while the upper ends of the stopper rods 66 are received in holes defined in the upper section 61 of the pile 1. The uppermost end of each of the stopper rods 66 is slightly enlarged, and a corresponding recess 68 is formed in the upper end of the hole receiving the associated stopper rod 66. Thus, the stopper rods 66 remain in the holes of the upper section 61 of the pile 1 until the inner and outer cylinders 52 and 53 are extended away from each other by more than a prescribed distance, and the heads of the stopper rods 66 are finally received in the recesses 68 defined on the upper surface of the flange 59 of the inner cylinder 53. Numeral 67 denotes metallic sleeves lining the holes provided in the upper section 61 of the pile 1 for receiving the upper ends of the stopper rods 66.

Figure 10:
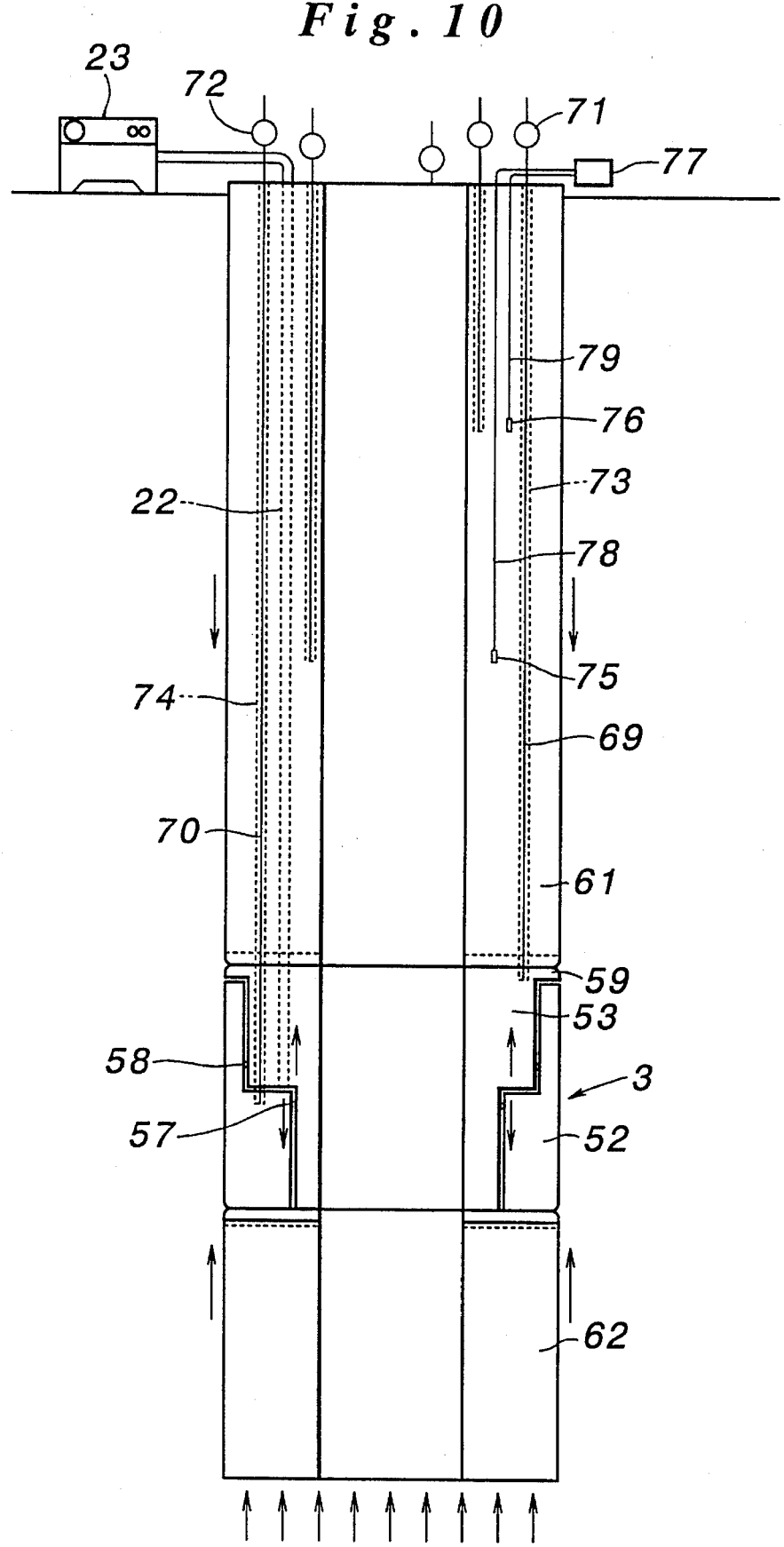
FIG. 10 is a sectional side view of a fifth embodiment of the present invention applied to a bored precast concrete pile.
Figure 11:
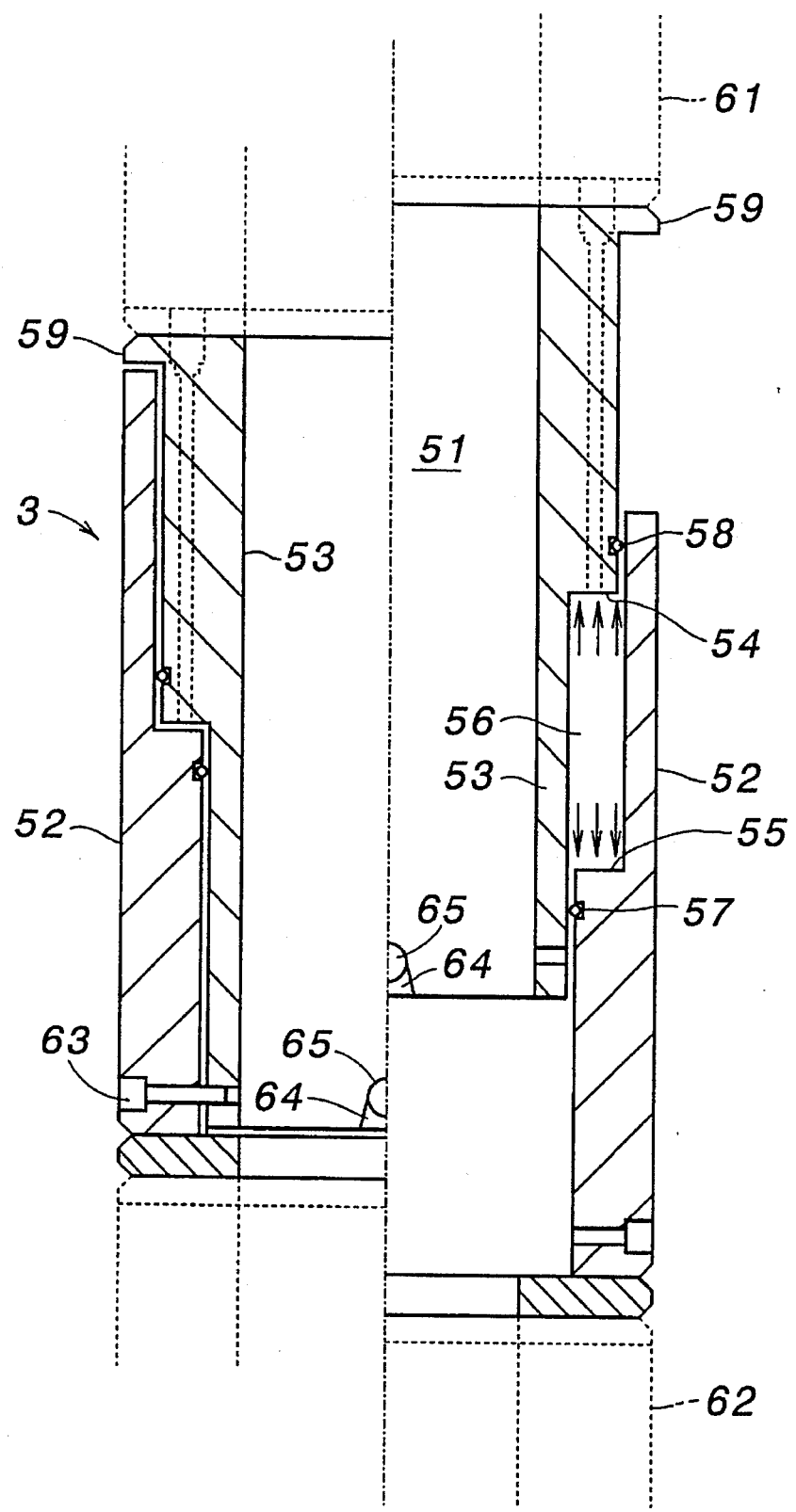
FIG. 11 is an enlarged sectional view showing a part of FIG. 10.

Referring to FIG. 10, lower ends of telltale rods 69 and 70 engage the upper surface of the flange 59 of the inner cylinder 53, and the upper end of the outer cylinder 52, respectively, and upper ends of these telltale rods 69 and 70 are connected to dial gages 71 and 72 placed on the ground surface to indicate the vertical displacements of the corresponding parts of the hydraulic cylinder assembly 3. These telltale rods 69 and 70 are guided by steel tubes 73 and 74 embedded in the concrete wall of the upper section 61 of the pile 1, and are hereby prevented from making direct contact with the concrete wall.

To measure the axial forces acting at various depths of the pile 1, rebar gages 75 and 76 are attached to desired locations of the pile 1 as illustrated in FIG. 10, and are electrically connected to a measuring instrument 77 placed on the ground surface via electric wires 78 and 79. A hydraulic feed hose 23 is embedded in the wall of the upper section 61 of the pile 1, and supplies hydraulic pressure delivered by a pump 23 on the ground surface to the annular cylinder chamber 56.

According to this embodiment, as hydraulic fluid supplied by the pump 23 is introduced into the annular chamber 56 via the feed hose 23, the shear bolts 63 are ruptured, and the inner and outer cylinders 52 and 53 are pushed apart away from each other. Initially, the lower end of the inner cylinder 53 is attached to the upper end of the lower section 62 of the pile 1 by concrete, and the detachment of the inner cylinder 53 from the upper end of the lower section 62 of the pile 1 can be detected by a sharp decline in the pressure in the hydraulic circuit due to the abrupt movement of the inner and outer cylinders 52 and 53 away from each other. At the same time, the displacements at various depths of the pile 1 as well as axial forces acting at various depths of the pile 1 are monitored by the associated measuring instruments. Thus, the bearing capacity of one of the sections of the pile can be measured by using the bearing capacity of the other section of the pile for supporting the hydraulic jack assembly 3 against the reaction force created by the application of the loading to the one section of the pile 1.

When the test for the bearing capacity of the pile has been completed, cement milk, resin mortar or other liquid which sets in time is introduced into the feed hose 22, and fills the entire hydraulic jack assembly 3. Obviously, this hydraulic jack assembly 3 can equally function even when it is inverted. Also, this embodiment can be applied to bored cast-in-place piles and steel piles as well with appropriate modifications.

In the previously described embodiments, it was possible to measure the bearing capacity of only one of the two sections of the pile located above and below the hydraulic jack assembly which has a smaller bearing capacity than the other. If the bearing capacity of each of the two sections is greater than the load producing capacity of the hydraulic jack assembly, it is possible only to determine that the bearing capacities of the two sections are greater than a value which is given by the maximum load producing capacity of the hydraulic jack assembly.

Figure 15:
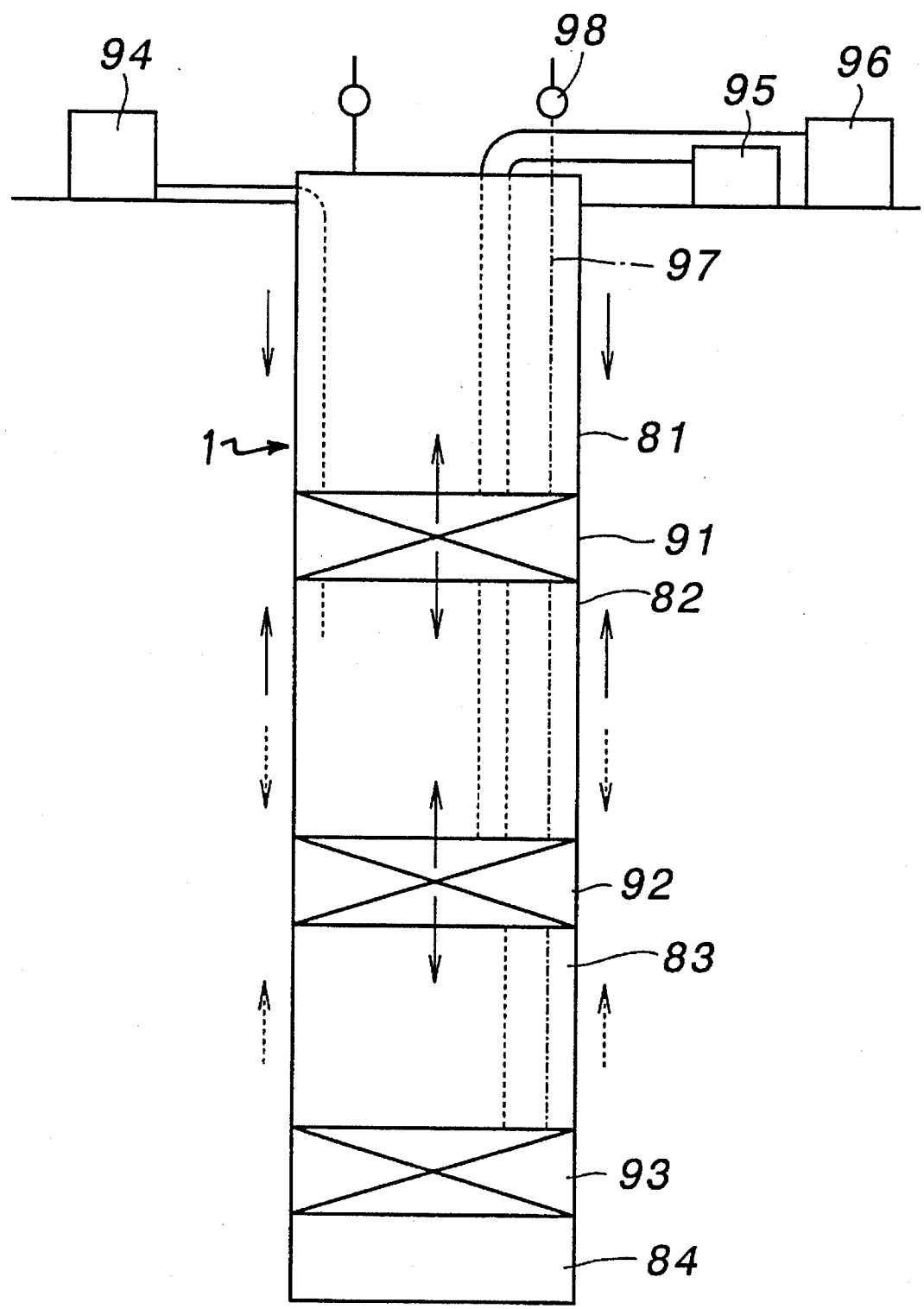
FIG. 15 is a diagram for illustrating a method for testing the bearing capacity of a pile according to the present invention.

FIG. 15 shows the method according to the present invention which allows more comprehensive evaluation of the bearing capability of a pile. The pile 1 is divided into four sections 81 through 84 although it can be divided into a different number of sections if desired. A hydraulic jack assembly is interposed between each pair of adjacent sections of the pile. As there are four sections of the pile, three hydraulic jack assemblies 91, 92 and 93 are used in this embodiment. Telltale rods extend from the ground surface to the upper ends of the associated hydraulic jack assemblies, and are connected to associated dial gages placed on the ground surface. The telltale rods and the dial gages are collectively denoted with numerals 97 and 98 in FIG. 15. Each of the hydraulic jack assemblies may consist of any one of the previously described hydraulic jack assemblies.

Three pumps 94, 95 and 96 are placed on the ground surface for individually controlling the hydraulic jack assemblies 91, 92 and 93, and conduits for feeding hydraulic fluid extend between the associated pumps and the associated hydraulic jack assemblies. It is also possible to use only one pump which feeds hydraulic fluid to the three hydraulic jack assemblies 91, 92 and 93, and to provide a pressure regulator for individually controlling the volume of the hydraulic fluid supplied to each of the hydraulic jack assemblies.

The mode of operation of this embodiment is described in the following. For the convenience of the description, the sections of the pile are referred to as first through fourth sections from above, and the hydraulic jack assemblies are referred to as first through third hydraulic jack assemblies likewise from above. In this embodiment, the uppermost section or the first section 81 of the pile is relatively long as compared to the remaining sections of the pile.

When the first hydraulic jack assembly 91 is pressurized, the second section 82 of the pile immediately below this hydraulic jack assembly is pushed downward with the reaction force of the hydraulic jack assembly supported by the shaft resistance of the first pile section 81 immediately above this hydraulic jack assembly. To accommodate this downward movement of the second section 82, the hydraulic fluid is drawn from the second jack assembly 92. It is thus possible to isolate and test the beating capacity of the second section 82 of the pile.

In a similar fashion, the bearing capacity of the third pile section 83 can be measured. In this case, the second hydraulic jack 92 is actuated and the reaction thereof is supported by the second section 82 while the downward movement of the third section 83 is accommodated by drawing hydraulic fluid from the third jack assembly 93. If the second section 82 is not sufficient to support the reaction of the second jack assembly 92, the first jack assembly 91 may be kept rigid so that the reaction force may be supported by both the first and the second sections 81 and 82.

Since the fourth pile section 84 or the lowermost pile section has a relatively small length, it is possible to directly measure the end bearing capacity of the pile by actuating the third hydraulic jack assembly 93, and using the shaft resistance and the weight of the three pile sections above the third hydraulic jack assembly 93 for supporting the reaction force of the third hydraulic jack assembly 93.

The bearing capacity of the first section 81 can be also measured because the downward reaction of the first hydraulic jack assembly 91 can be supported by the three sections 82, 83 and 84 of the pile therebelow. In this case, the maximum load that will be applied by the first hydraulic jack assembly 91 is given as a sum of the weight of the first section 81 of the pile and the total shaft resistance acting thereon.

FIG. 16 shows the performance of a pile consisting of three pile sections 100, 101 and 102 and a pair of hydraulic jack assemblies 103 and 104 interposed between each adjacent pair of the pile sections. FIG. 16 (a) illustrates the constitution of the soil, and FIG. 16 (b) shows the general structure of this pile. In FIG. 16 (c), the solid lines show the distribution of the axial force along the length of the pile when the first hydraulic jack assembly 103 is actuated for applying a force which tends to move the first and second pile sections 100 and 101 away from each other while the actuation of the second hydraulic jack assembly 104 is regulated so as to produce a constant axial force at the second hydraulic jack 104. The dotted lines indicate the distribution of the axial force when the second hydraulic jack assembly 104 is actuated for applying a force which tends to move the second and third pile sections 101 and 102 away from each other while the actuation of the first hydraulic jack assembly 103 is likewise regulated so as to produce a constant axial force at the first hydraulic jack 103. FIG. 16 (d) is a graph similar to FIG. 16 (c) showing the distribution of the axial force when only one of the hydraulic jack assemblies is actuated without regulating the actuation of the remaining hydraulic jack assembly or while keeping the remaining jack assembly rigid during the test. By thus regulating the axial forces at the jack assemblies as indicated in FIG. 16 (c), it is possible to test the different sections of the pile without involving any excessive displacements of the associated sections.

Figure 17:
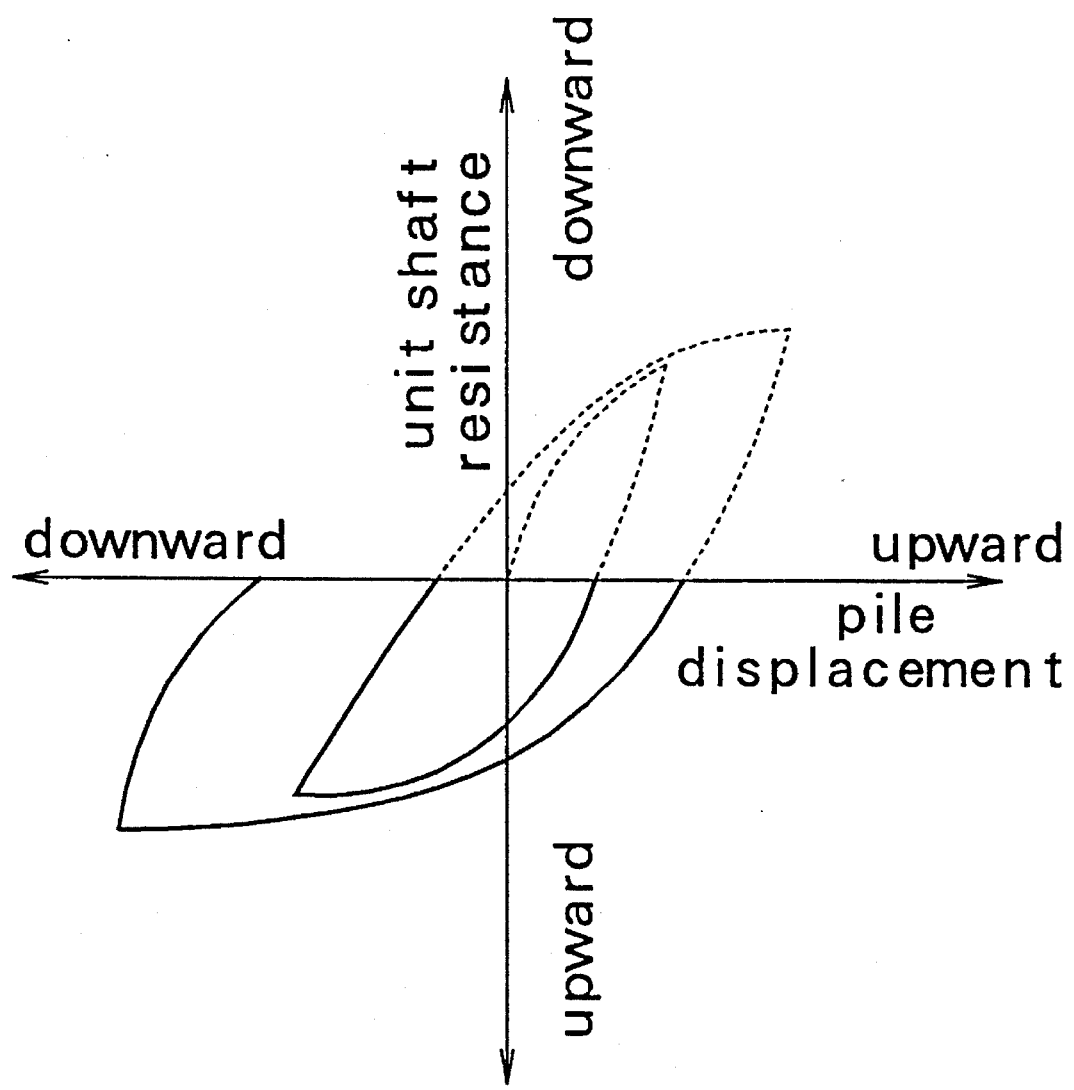
FIG. 17 is a graph showing the relationship between the reciprocating unit shaft resistance, and the displacement of the pile.

To more accurately evaluate the performance of a pile under an oscillatory load which may be encountered, for instance, when the pile is loaded by an earthquake or by wind, it is desirable to apply a reciprocating testing load to a pile. FIG. 17 is a graph showing the relationship between the reciprocating load acting on the middle section of the pile and the resulting displacement thereof. According to the present embodiment, it is possible to apply a reciprocating load to any middle section of a pile consisting of three or more sections by alternatingly introducing hydraulic fluid into one of the hydraulic jack assemblies located above and below the pile section in question while drawing hydraulic fluid from the other jack assembly by equal amount even through the hydraulic jack assemblies are single acting cylinders which are only capable of extending, and are not capable of retracting by themselves under hydraulic pressure. The solid lines and the dotted lines represent the forces applied by the upper and lower hydraulic jack assemblies, respectively.

Figure 18:
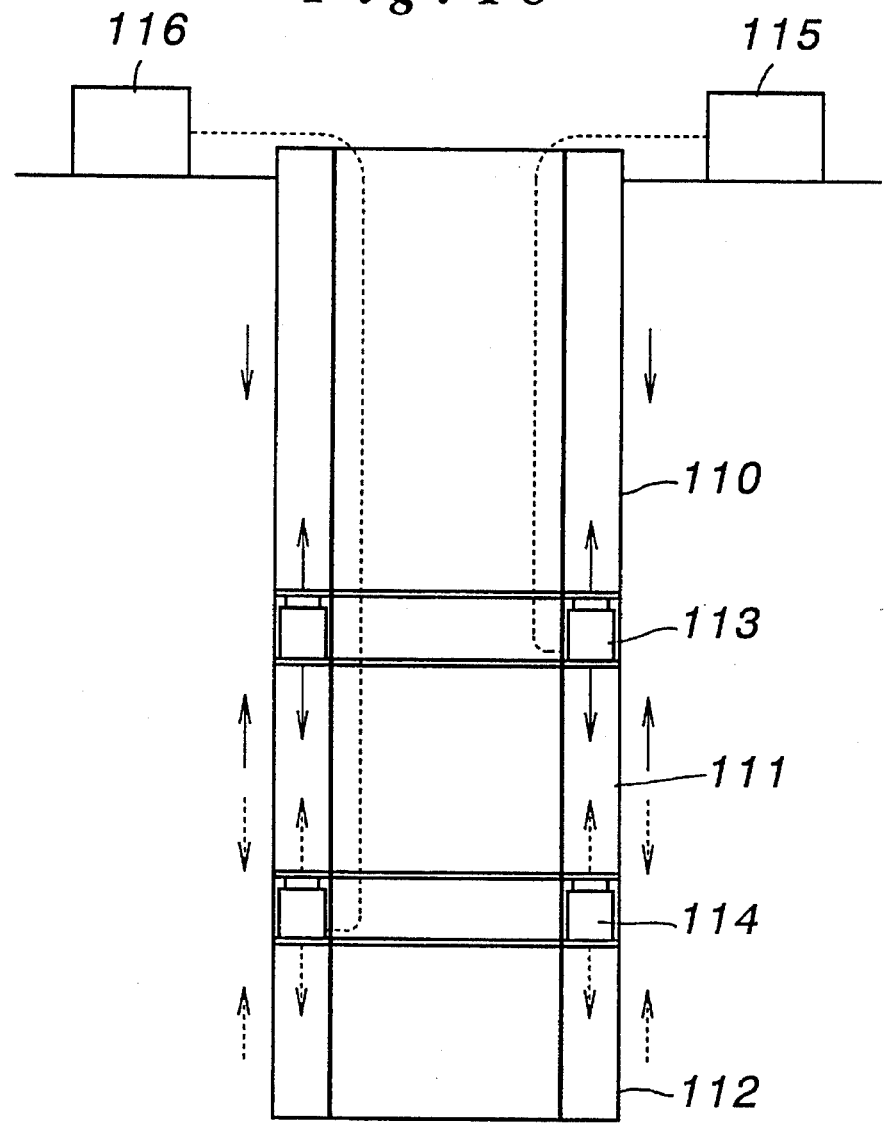
FIG. 18 shows an alternate arrangement for implementing the method of the present invention.
Figure 19:
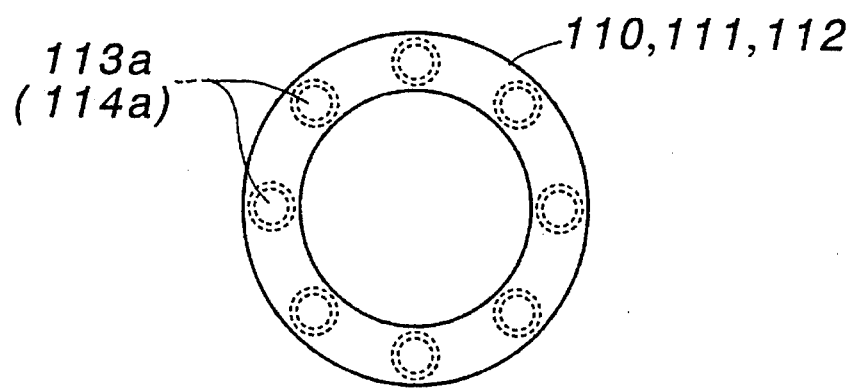
FIG. 19 is a cross sectional view of the hydraulic jack assembly used in the embodiment of FIG. 18.

FIGS. 18 and 19 illustrate an embodiment applied to a pile consisting of three sections 110, 111 and 112, and a pair of hydraulic jack assemblies 113 and 114 interposed between adjacent pairs of the pile sections. Each of the hydraulic jack assemblies 113 and 114 consists of a plurality of individual hydraulic jacks 113a and 114a each of which is provided with a flow rate regulating valve so that the individual hydraulic jacks can be lifted uniformly even when the pile is subjected to asymmetric unit shaft resistance. The individual hydraulic jacks 113a and 114a may consist of a common cylinder and ram arrangement or a bellows type arrangement illustrated in FIG. 5.

Alternatively, each of the hydraulic jack assemblies may consist of an annular cylinder and ram arrangement illustrated in FIGS. 11 through 14.

Figure 20:
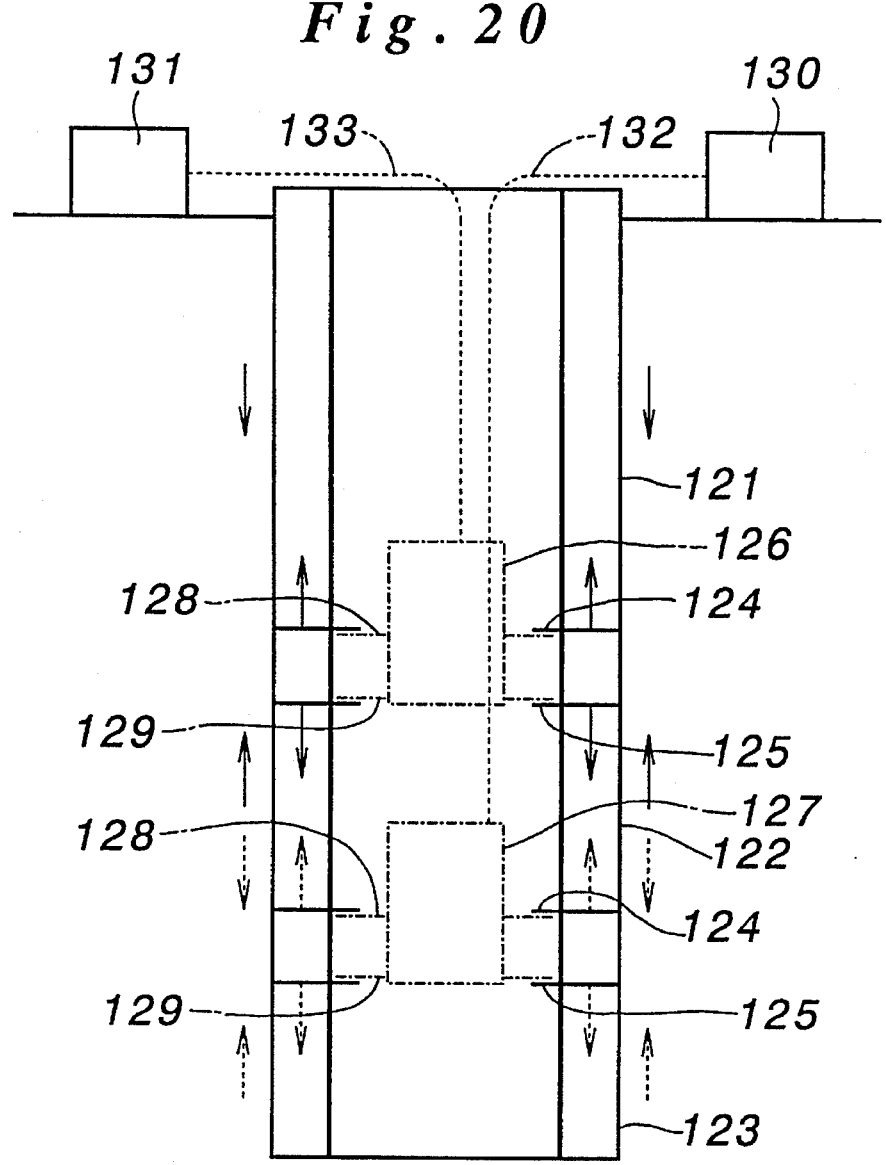
FIG. 20 is a cross sectional view of yet another alternate arrangement for implementing the method of the present invention.
Figure 21:
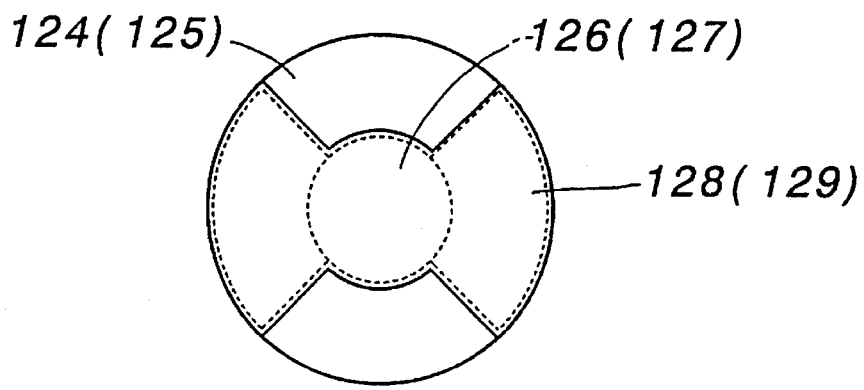
FIG. 21 is a cross sectional view of the hydraulic jack assembly used in the embodiment of FIG. 20.

FIGS. 20 and 21 show yet another embodiment of the present invention using a plurality of hydraulic jack assemblies 126 and 127 for testing a pile consisting of three or more sections 121, 122 and 123. In this case, the pile is generally hollow, and is provided with a pair of diagonally opposing fan-shaped flanges 124 and 125 at each terminal end of each of the pile sections. A pair of hydraulic jacks 126 and 127 are suspended from the ground surface, and are each provided with a pair of diagonally opposing fan-shaped flanges 128 and 129 on each working end thereof so that each of the hydraulic jacks may be selectively engaged with the associated flanges 124 and 125 of the pile sections by appropriately turning the flanges 128 and 129 of the hydraulic jack assemblies 126 and 127 relative to the flanges 124 and 125 provided in the pile sections, and may be interposed between an associated adjacent pair of the pile sections. These hydraulic jack assemblies receive hydraulic fluid from pumps 130 and 131 on the ground surface via conduits 132 and 133 extending between the pumps and the hydraulic jacks.

In this case, after the test has been completed, the hydraulic jack assemblies can be recovered, and may be used repeatedly for testing other piles. In the illustrated embodiment, two hydraulic jack assemblies are used, but it is also possible to use only one hydraulic jack assembly, and engage it with each of a plurality of points in the same pile in a sequential manner.

Although the present invention has been described in terms of specific embodiments, it is possible to modify and alter details thereof without departing from the spirit of the present invention. For instance, the jack assemblies used in the above described embodiments consisted of hydraulic jacks, but may also consist of any powered jacks which may be mechanically, electrically or otherwise actuated. The piles are not limited to concrete cast piles, but may also consist of steel piles, wood columns, or other piles made of any suitable material.

What we claim is:

1. A device for testing the bearing capacity of a pile placed in an earthen shaft, comprising:

a hydraulic jack assembly interposed between at least a pair of adjacent upper and lower sections of said pile;

means for supplying hydraulic fluid to said hydraulic jack assembly;

means for measuring displacements of an upper end and a lower end of said hydraulic jack assembly; and means for measuring an axial force acting on said pile;

said hydraulic jack assembly defining a hollow center allowing material to be transferred between said adjacent sections of said pile.

2. A device for testing a bearing capacity of a pile according to claim 1, wherein said hydraulic jack assembly comprises a plurality of individual hydraulic jacks arranged around an axial center of said pile.

3. A device for testing a bearing capacity of a pile according to claim 2, further comprising flow regulating means for feeding said hydraulic fluid uniformly to each of said hydraulic jacks.

4. A device for testing a bearing capacity of a pile according to claim 2, wherein said pile consists of a bored cast-in-place concrete pile reinforced by a rebar cage, and said hydraulic jack assembly is interposed between a pair of annular plates which are securely attached to an upper section and a lower section of said rebar cage, respectively.

5. A device for testing a bearing capacity of a pile according to claim 4, wherein said upper and lower annular plates are connected with each other by tension rods which are adapted to be ruptured by a relatively small axial force produced from said hydraulic jack assembly.

6. A device for testing a bearing capacity of a pile according to claim 4, wherein each of said hydraulic jacks is supported by one of said upper and lower annular plates by way of a spherical seat at one end thereof.

7. A device for testing a bearing capacity of a pile according to claim 4, wherein said upper and lower annular plates are provided with a pair of annular separator plates, and bellows are placed across inner and outer edges of said separator plates to keep off concrete away from moveable parts of said hydraulic jack assembly.

8. A device for testing a beating capacity of a pile according to claim 4, wherein rebars secured to one of said annular plates are passed through openings provided in a part of the other of said annular plates, and lower ends of conduits adapted to receive cement milk or resin mortar from a ground surface are fitted on said rebars.

9. A device for testing a bearing capacity of a pile according to claim 8, wherein said rebars are passed through openings provided in an associated one of said annular separator plates.

10. A device for testing a bearing capacity of a pile according to claim 1, wherein said hydraulic jack assembly comprises inner and outer cylinders having annular shoulder surfaces on mutually opposing sides thereof and being disposed in a mutually slidable manner in a coaxial arrangement, thereby defining an annular cylinder chamber therebetween.

11. A device for testing a beating capacity of a pile according to claim 10, wherein said inner and outer cylinders are engaged by shear or tension pins to prevent sagging of a lower end of said cylinder assembly under the weight of a section of said pile located under said hydraulic jack assembly.

12. A device for testing a bearing capacity of a pile according to claim 10, wherein said inner and outer cylinders are engaged by radial pins passed through holes provided in one of said inner and outer cylinders, and received by notches provided in the other of said inner and outer cylinders, said notches opening toward a lower end of the associated cylinder so that said radial pins prevent relative rotation between said inner and outer cylinders in a retracted state of said hydraulic jack assembly without restricting extension of said hydraulic jack assembly.

13. A device for testing a bearing capacity of a pile according to claim 10, wherein said displacement measuring means comprises a telltale rod having a lower end engaged by a part of said pile, and an upper end connected to a dial gage for measuring an axial movement of said telltale rod relative to a fixed point of reference.

14. A method for testing the beating capacity of a pile placed in an earthen shaft, comprising the steps of:

placing a pile in an earthen shaft with a hydraulic jack assembly for applying an axial load placed at an arbitrary point of said pile;

placing measuring means in association with said hydraulic jack assembly for measuring a displacement and an axial force of said hydraulic jack;

arranging a plurality of displacement or strain gages in different parts of said pile located above said hydraulic jack;

extending said hydraulic jack assembly;

measuring the displacement and the axial force of said hydraulic jack assembly and obtaining readings from said displacement or strain gages;

computing a unit shaft resistance of a plurality of points of said pile above said hydraulic jack from said displacement and axial force of said hydraulic jack and said displacement or strain readings; and determining an axial force and a displacement of each point of said pile when said pile is loaded at an upper end thereof according to a load transfer analysis.

15. A method for testing the bearing capacity of a pile placed in an earthen shaft, comprising the steps of:

placing a pile consisting of at least three sections in an earthen shaft;

interposing at least a pair of hydraulic jack assemblies each between an adjacent pair of said pile sections; and simultaneously actuating said pair of hydraulic jack assemblies to test a load supporting capacity of one of said pile sections located between said hydraulic jack assemblies without being interfered by axial forces or displacements of other pile sections.

16. A method for testing the bearing capacity of a pile placed in an earthen shaft, comprising the steps of:

placing a pile consisting of at least three sections in an earthen shaft;

interposing at least a pair of single acting hydraulic jack assemblies each between an adjacent pair of said pile sections; and alternatingly actuating said pair of hydraulic jack assemblies to apply a reciprocating load to one of said pile sections located between said hydraulic jack assemblies.

17. A device for testing a bearing capacity of a pile according to claim 1 wherein said pile is a hollow cylinder pile having a circumferential wall and wherein said hydraulic jack assembly is coextensive with said circumferential wall.

* * * * *

UNITED STATES PATENT AND TRADEMARK OFFICE
CERTIFICATE OF CORRECTION

PATENT NO. : 5,608,169
DATED : March 4, 1997
INVENTOR(S) : FUJIOKA et al

It is certified that error appears in the above-indentified patent and that said Letters Patent is hereby corrected as shown below:

Col. 14, line 13, "beating" should read --bearing--; and line 52, "beating" should read --bearing--.

Signed and Sealed this

Thirteenth Day of January, 1998

Attest:

BRUCE LEHMAN

Attesting Officer

Commissioner of Patents and Trademarks